US012781132B2

(12) United States Patent
Moors et al.

(10) Patent No.: US 12,781,132 B2

(45) Date of Patent: Nov. 3, 2026

(54) PRODUCTION OF SYNTHETIC HYDROCARBONS

(71) Applicant: Arcadia eFuels US Inc.

(72) Inventors: Jeroen Harrie Moors, Kuching (MY); Andrew John Tolan, Christchurch (NZ); Brendon Bruce Miller, Christchurch (NZ)

(73) Assignee: Arcadia eFuels US Inc., Austin, TX (US)

( * ) Notice: Subject to any disclaimer, the term of this patent is extended or adjusted under 35 U.S.C. 154(b) by 61 days.

(21) Appl. No.: 18/203,472

(22) Filed: May 30, 2023

(65) Prior Publication Data

US 2024/0400908 A1 Dec. 5, 2024

(51) Int. Cl.

| | |
|---|---|
| ***C10G 2/00*** | (2006.01) |
| ***C02F 11/04*** | (2006.01) |
| ***C02F 103/08*** | (2006.01) |
| ***C10G 45/58*** | (2006.01) |
| ***C10G 47/00*** | (2006.01) |

(Continued)

(52) U.S. Cl.

CPC ................ *C10G 2/50* (2013.01); *C02F 11/04* (2013.01); *C10G 45/58* (2013.01); *C10G 47/00* (2013.01); *C10L 3/12* (2013.01); *C12M 21/04* (2013.01); *C25B 1/04* (2013.01); *C25B 15/081* (2021.01); *C25B 15/085* (2021.01);

(Continued)

(58) Field of Classification Search

CPC ....................................................... C25B 1/04

See application file for complete search history.

(56) References Cited

U.S. PATENT DOCUMENTS

| | | | |
|---|---|---|---|
| 11,111,195 | B2 | 9/2021 | MacGregor |
| 11,857,938 | B2 | 1/2024 | Schuetzle et al. |

(Continued)

FOREIGN PATENT DOCUMENTS

| | | | | |
|---|---|---|---|---|
| EP | 3156519 A1 * | 4/2017 | ............... | C10G 2/50 |
| WO | WO-2010039320 A2 * | 4/2010 | .............. | F01K 7/22 |

(Continued)

OTHER PUBLICATIONS

International Search Report and Written Opinion associated with PCTUS2024029590 which is the foreign counterpart of U.S. Appl. No. 18/203,472.

*Primary Examiner* — Ciel P Contreras

(74) *Attorney, Agent, or Firm* — Reid Law Practice PLLC; Frank E. Reid

(57) ABSTRACT

An eFuels plant and process for producing synthetic hydrocarbons using renewable energy are disclosed. The eFuels plant comprises a hydrocarbon synthesis (HS) system and a renewable feed and carbon/energy recovery (RFCER) system. The RFCER comprises an electrolysis unit to convert water to hydrogen and oxygen. The hydrogen and carbon dioxide are fed to the HS system to produce synthetic hydrocarbon products. The process further comprises a thermal desalination unit, a direct air capture unit, an oxygen-fired heater, a steam turbine generator, a heat recovery unit, anaerobic and/or aerobic wastewater treatment, or a combination thereof. Process streams of and heat generated in the HS and RFCER systems are integrated to improve energy, hydrogen, and carbon efficiency and maintain stable operations during power fluctuations to the eFuels plant.

29 Claims, 4 Drawing Sheets

(51) Int. Cl.

| | |
|---|---|
| ***C10L 3/12*** | (2006.01) |
| ***C12M 1/107*** | (2006.01) |
| ***C12P 5/02*** | (2006.01) |
| ***C25B 1/04*** | (2021.01) |
| ***C25B 15/08*** | (2006.01) |

(52) U.S. Cl.

CPC ...... *C02F 2103/08* (2013.01); *C10G 2400/02* (2013.01); *C10G 2400/08* (2013.01); *C12P 5/023* (2013.01)

(56) References Cited

U.S. PATENT DOCUMENTS

| | | | | |
|---|---|---|---|---|
| 2011/0008736 | A1* | 1/2011 | Arai | B01F 25/3131 44/457 |
| 2019/0185396 | A1* | 6/2019 | Schulz | F25J 3/0223 |
| 2020/0208274 | A1 | 7/2020 | Gorse et al. | |
| 2021/0261010 | A1 | 8/2021 | Pickles et al. | |
| 2021/0292664 | A1 | 9/2021 | Chishima | |
| 2021/0340076 | A1* | 11/2021 | Schuetzle | C10G 2/32 |
| 2021/0340077 | A1 | 11/2021 | Schuetzle et al. | |
| 2022/0064541 | A1* | 3/2022 | Lyubovsky | B01D 3/007 |
| 2022/0112429 | A1 | 4/2022 | Greager et al. | |
| 2022/0333015 | A1 | 10/2022 | Mcginnis et al. | |
| 2022/0401909 | A1 | 12/2022 | Chishima | |
| 2022/0403536 | A1 | 12/2022 | Chishima | |
| 2023/0012800 | A1 | 1/2023 | Mortensen et al. | |
| 2023/0079115 | A1 | 3/2023 | Bank et al. | |
| 2023/0107017 | A1* | 4/2023 | Gilliam | C25B 15/02 205/337 |
| 2023/0119589 | A1* | 4/2023 | Darcy | C10J 3/82 585/242 |
| 2023/0242822 | A1 | 8/2023 | Schuetzle et al. | |
| 2023/0243048 | A1* | 8/2023 | McWaid | C25B 9/19 205/637 |
| 2023/0406793 | A1 | 12/2023 | Obrist | |
| 2024/0076789 | A1* | 3/2024 | Snoswell | C25B 1/042 |

FOREIGN PATENT DOCUMENTS

| | | | | |
|---|---|---|---|---|
| WO | 2019228809 | A1 | 12/2019 | |
| WO | 2021083897 | A1 | 5/2021 | |
| WO | 2022096615 | A1 | 5/2022 | |
| WO | 2022112642 | A1 | 6/2022 | |
| WO | 2022140558 | A2 | 6/2022 | |
| WO | 2022171643 | A1 | 8/2022 | |
| WO | 2022200315 | A1 | 9/2022 | |
| WO | WO-2022223458 | A1 * | 10/2022 | C01B 3/38 |
| WO | 2022245844 | A1 | 11/2022 | |
| WO | WO-2023036560 | A1 * | 3/2023 | C25B 1/04 |
| WO | 2023138876 | A1 | 7/2023 | |
| WO | 2023172346 | A1 | 9/2023 | |

* cited by examiner

PRODUCTION OF SYNTHETIC HYDROCARBONS

FIELD OF THE INVENTION

This disclosure relates to the production of synthetic hydrocarbons. More particularly, the disclosure relates to synthesis of sustainable liquid hydrocarbons from sea water, renewable electricity, and carbon dioxide.

BACKGROUND OF THE INVENTION

The vast majority of vehicles worldwide are powered by hydrocarbon fuels, including automobiles, ships, aircraft, and trains. This demand for hydrocarbon fuels is supplied by a global infrastructure of production and distribution. Global efforts to reduce carbon dioxide emissions associated with hydrocarbon fuel consumption have included combinations of electrolysis, autothermal reforming, and Fischer-Tropsch technologies, sometimes in combination with electricity from renewable sources, to synthesize hydrocarbon fuels. These technologies are often implemented in ways that reduce carbon dioxide ($CO_2$) to the environment with a goal of creating a $CO_2$ neutral production and use cycle.

However, operation of implementations of these technologies still requires use of electrical power. With more renewable energy coming on stream on the electricity grid, the stability of the grid is becoming more critical. Renewable energy production fluctuates with wind/solar conditions and at the same time grid demand fluctuates depending on the time of the day and/or time of year. A facility for production of synthetic fuels is a relatively large demand center on the electrical grid servicing such a facility.

There is a need to provide improved processes to produce hydrocarbon fuels sustainably, wherein such processes have a higher overall energy efficiency, a net lower carbon footprint and/or operate to help stabilize the electrical grid. Ideally, such processes would be highly flexible and could be implemented with commonly used equipment and familiar techniques to produce a wide variety of products.

SUMMARY OF THE INVENTION

In some embodiments, a process for producing one or more synthetic hydrocarbon products is implemented in an eFuels plant, comprising a hydrocarbon synthesis (HS) system and a renewable feed and carbon/energy recovery (RFCER) system. The RFCER system comprises a feed system producing hydrogen and carbon dioxide feed streams to the HS system. In some embodiments, the eFuels plant further comprises one or more of a thermal desalination unit, a direct air capture unit, a hydrogen storage system (and optionally a hydrogen compression system), a carbon dioxide compression and storage system, an oxygen-fired heater, a steam turbine generator, an anaerobic biodigestion unit, and an aerobic biodigestion unit. In some embodiments, the eFuels plant comprises an anaerobic biodigestion unit and an aerobic biodigestion unit. The feed system and the other processing units of the RFCER system are integrated with processes within the HS system and with each other to minimize the carbon footprint of the eFuels plant, to maximize energy efficiency of the eFuels plant (i.e., minimize the amount of energy required from external sources for operation of the eFuels plant), to maximize hydrogen and carbon efficiency of the eFuels plant, to support electrical grid frequency stability, and to maximize operating flexibility to permit continued operations in spite of fluctuations in power available from the electrical grid supplying power to the eFuels plant.

In some embodiments, the process for producing one or more synthetic hydrocarbon products comprises introducing electricity and a water feed stream to an electrolysis unit under reaction conditions sufficient to form a hydrogen stream and an oxygen stream, wherein the electrolysis unit comprises one or more alkaline electrolysis cells (AECs) and/or one or more proton exchange membrane cells (PEMs). The PEMs and/or AECs are selected to provide a balance between energy efficiency and operating flexibility by having the ability to respond to fluctuations in the electrical grid, or said another way, to provide grid stabilization by reducing the electrical power demand of the eFuels plant during periods of peak demand on the electrical power grid). Such periods of peak power demand can result from supply side limitations, such as intermittency of renewable energy sources, demand side increases, such as instantaneous and/or seasonal weather conditions, or a combination thereof.

In some embodiments, the electricity required to operate the eFuels plant is in the range of from 50 MW to 4,000 MW, from 100 MW to 500 MW, from 275 MW to 425 MW, or from 325 MW to 375 MW. The eFuels plant total electricity requirements can be compartmentalized as the load for the electrolysis unit (Zone 1) and the eFuels plant other than the electrolysis unit (Zone 2). In some embodiments Zone 1 is a separate adjacent facility. In some embodiments, the load for Zone 1 is in the range of from 62% to 79%, from 64% to 77%, or from 68% to 73%, and the load for Zone 2 is in the range of from 21% to 38%, from 23% to 36%, or from 27% to 32%, wherein the combined load for Zone 1 and Zone 2 is 100%. The RFCER system total electricity requirements can be compartmentalized as the load for the electrolysis unit (Zone 1a) and the RFCER system other than the electrolysis unit (Zone 2a). In some embodiments, the load for Zone 1a is in the range of from 72% to 90%, from 74% to 88%, from 76% to 86%, or from 78% to 84%, and the load for Zone 2a is in the range of from 10% to 28%, from 12% to 26%, from 14% to 24%, or from 16% to 22%, wherein the combined load for Zone 1a and Zone 2a is 100%. Regardless of how the electrical load requirements of the eFuels plant are broken down, the foregoing ranges show that the electrolysis unit is a major portion of the overall electrical load. Hence, an ability to control the electrical demand of the electrolysis unit is significant for response to fluctuations in the electrical grid providing power to an eFuels plant, thereby providing needed stabilization for the grid.

Grid stabilization can be generally categorized based on the required speed of response, such as, but not limited to, 0 to 10 seconds, 1 second to 2 minutes, 10 seconds to 5 minutes, and 30 seconds to 20 minutes. A battery can respond immediately up to its available charged capacity, i.e., 0 to 5 seconds or 0 to 10 seconds (i.e., substantially instantaneous to 10% of total charged capacity/sec or instantaneous to 20% of total charged capacity/sec), and is therefore a useful control means for any of the aforementioned response time intervals either alone or in combination with other control steps. The available charged capacity is dependent upon the total battery capacity and management of eFuels plant operations to store electrical energy in such total battery capacity. In some embodiments, total battery capacity is in the range of from 5 MW·hr to 50 MW·hr, or alternatively 2% to 20% of maximum electrical load of the electrolysis unit for 1 hour, or alternatively sufficient electrical power to operate the electrolysis unit at full load for up to 15 minutes. Atmospheric AEC electrical loads can be increased or decreased at a rate of 5 to 10 seconds per percent of electrical load (i.e., 0.1% electrical load/sec to 0.2% electrical load/sec), based on 100% being the maximum atmospheric AEC electrical load. Electrical loads for pressurized AECs and/or PEMs, such as, but not limited to 30 barg to 40 barg, can be increased or decreased at a rate of 0.25 to 1 second per percent of electrical load (i.e., 1% electrical load/sec to 4% electrical load/sec), based on 100% being the maximum pressurized AECs and/or PEMs electrical load. In some embodiments, grid stabilization can be achieved in all four response time categories (i.e., 0 to 10 seconds, 1 second to 2 minutes, 10 seconds to 5 minutes, and 30 seconds to 20 minutes) with the battery responding first, followed by the faster acting pressurized AEC and/or PEM electrolyzers, and finally by the slower acting atmospheric AECs.

An increase or reduction in electrolysis unit electrical load leads to a corresponding increase or reduction in production of a hydrogen feed. Since hydrogen is a major feed stream to one or more process units in the HS system, a change in the rate of hydrogen supplied to the HS system will result in changes to the operation of such one or more process units in the HS system. The production rates of affected process units in the HS system would have to increase or decrease according to the rates of hydrogen supplied to the HS system. In some instances, a higher rate of change and/or the magnitude of change of the amount of hydrogen supplied to the HS system may exceed the response capabilities of one or more affected process units, resulting in operational upsets to or even shutdown of the affected process units.

In some embodiments, the required changes to HS system operation triggered by changes in electrolysis unit hydrogen production rates are mitigated or eliminated by decoupling the HS system from direct dependence on electrolysis unit hydrogen production rates through the use of hydrogen storage. In some embodiments, when conditions favor maximizing electrolysis unit rates (e.g., available electricity at lower cost) to an extent that hydrogen is produced in excess of HS system requirements, the excess hydrogen is inventoried in a hydrogen storage system. In some embodiments, when conditions favor reducing electrolysis unit rates (e.g., limited electricity available from the grid and/or higher electricity cost) to an extent that hydrogen is produced is less than HS system requirements, the hydrogen inventoried in the hydrogen storage system is withdrawn to offset the shortfall. Furthermore, in some embodiments, when electrolysis unit hydrogen production rates are unintentionally reduced due to fluctuations in electricity from the grid and/or unexpected rate reduction or shutdown of all or a portion of the electrolysis unit hydrogen capacity, hydrogen withdrawn from storage is immediately available to offset the reduced production of hydrogen.

In some embodiments, one of the products produced from the HS system is synthesized liquid gas (SLG), which comprises substantially the same constituents as liquefied petroleum gas (LPG) but is not derived from a petroleum source. As a product from the HS system, SLG is inventoried in an SLG storage system to the extent it is not being recycled to the HS system and/or withdrawn as a product for sale. In some embodiments, SLG can be withdrawn from the SLG storage system and fed to one or more process units in the HS system (e.g., a reverse water-gas shift reactor) to offset an intentional or unintentional reduction in hydrogen produced and fed to the HS system. In some embodiments, SLG is intentionally fed to the HS system to reduce hydrogen consumed by the HS system, thereby allowing hydrogen to be routed to the hydrogen storage system.

The process further comprises feeding at least a portion of the hydrogen stream and a carbon dioxide stream to the HS system. Hydrocarbon synthesis conditions are implemented in the HS system sufficient to produce synthetic hydrocarbon products. Synthetic hydrocarbon products are recovered, including one or more of a synthetic liquefied gas (SLG), a synthetic light distillate (SLD), a synthetic middle distillate (SMD), and a synthetic heavy distillate (SHD).

In some embodiments, the carbon dioxide stream is derived from one or more of importing carbon dioxide from a source external to the RFCER system (e.g., pipeline from an adjacent or remote facility or delivery by truck, rail, and/or ship to a carbon dioxide storage system within the RFCER system), anaerobic digestion of biomass for recovering carbon dioxide, anaerobic digestion of process water streams recovering carbon dioxide, and/or combusting biomass recovering carbon dioxide. In some embodiments, in addition to or in place of the forgoing, the RFCER system further comprises a direct air capture (DAC) unit to recover carbon dioxide to feed to the HS system.

In some embodiments, a hydrogen compression system supplies high-pressure hydrogen to the hydrocarbon synthesis system and/or a high-pressure hydrogen storage system. The high-pressure storage system provides an inventory of high-pressure hydrogen to supplement or replace hydrogen produced by the hydrogen compression system when the production of high-pressure hydrogen is intentionally or unintentionally either reduced or shut down. Alternatively, in some embodiments, a high-pressure electrolyzer supplies high-pressure hydrogen to the hydrocarbon synthesis system and/or a high-pressure hydrogen storage system without the need for a high-pressure compression system or requiring a compression system of reduced scale and scope. In such embodiments, the water fed to the electrolyzers is pressurized by pump capacity upstream of the electrolyzers, thereby eliminating or reducing the need to further pressurize the hydrogen produced from the electrolyzers.

In some embodiments, a carbon dioxide compression system supplies high pressure carbon dioxide to the HS system and/or a high-pressure carbon dioxide storage system. Process conditions for the high-pressure carbon dioxide can range from a liquid phase appropriate conditions to reach liquid phase including a temperature of −50° C. and a pressure of 7 barg or appropriate conditions to reach gas phase including a temperature of 25° C. and a pressure of 40 barg. The high-pressure carbon dioxide storage system provides an inventory of high pressure carbon dioxide to supplement or replace carbon dioxide produced by the carbon dioxide compression system when operation of the carbon dioxide compression system is either limited or shut down due to fluctuations in the $CO_2$ supply and/or the electrical power grid supplying electricity to the eFuels plant.

In some embodiments, a synthetic liquefied gas (SLG) pump system supplies pressurized SLG to the hydrocarbon synthesis system and/or a pressurized SLG storage system. While SLG may be stored at a pressure in the range of from 2 barg to 10 barg, the HS system would require an SLG feed pressure in the range of from 30 barg to 40 barg. The pressurized storage system provides an inventory of pressurized SLG to supplement feed to processes within the HS system, such as a reverse water-gas shift reactor, and/or the RFCER system, such as the oxygen-fired heater (OFH).

In some embodiments, the process further comprises obtaining a water feed to the electrolysis unit by adding sea water to a thermal desalination unit under desalination conditions to produce a desalinated water effluent and adding the desalinated water effluent to a demineralization unit under demineralization conditions to produce a demineralized water effluent as a feed to the electrolysis unit and/or a feed to a deaeration unit wherein deaeration conditions are implemented to produce boiler feedwater. In some embodiments, boiler feedwater is provided to the HS system for use as a cooling medium to other processes within the HS system and then returned to the RFCER system as steam.

In some embodiments, the process further comprises adding combustion reactants to the combustion zone of an OFH, comprising a combustion zone and a heating zone. The combustion reactants comprise oxygen from the electrolysis unit and a fuel gas stream comprising one or more of HS system purge gas, HS system off gas, and SLG withdrawn from the HS system and/or the SLG storage system. The combustion reactants are combusted in the combustion zone to produce heat and a flue gas comprising carbon dioxide. The use of oxygen instead of air reduces the concentration of inerts (e.g., nitrogen) in the flue gas exiting the combustion zone, thereby making recovery of the $CO_2$ more energy efficient and preventing the formation of combustion byproducts including nitrogen oxide ($NO_X$) compounds. The recovered $CO_2$ is sent to one or more process units in the HS system, such as a reverse water-gas shift reactor, as an additional source of carbon dioxide feed from the RFCER system.

In some embodiments, one or more steam streams are withdrawn from the HS system and introduced to the heating zone of the oxygen-fired heater, wherein a portion of the heat produced in the combustion zone is transferred to the heating zone to produce superheated steam. Superheated steam withdrawn from the heating zone can be used to drive a steam turbine generator, which extracts energy from the superheated steam to produce generated electricity and steam condensate. The generated electricity is used to supply or supplement the power requirements of the RFCER system and/or the HS system. The steam condensate is processed for use as additional water feed to the electrolysis unit. In another embodiment the energy extracted from the OFH heating zone can also be used to provide heat to the HS system.

In some embodiments, the process further comprises withdrawing a process wastewater stream, comprising a first organic material, from the HS system as feed to an anaerobic biodigester. Anaerobic biodigestion conditions are implemented in the anaerobic biodigester to convert the process wastewater stream to a first gas product stream and a first treated water stream. The first gas product stream comprises carbon dioxide, methane, or a combination thereof, and is purified to the relevant HS system feed specification, compressed, and recycled to the HS system for use as feed to and/or fuel for one or more process units in the HS system, thereby improving carbon, hydrogen, and/or energy efficiency.

In some embodiments, the process further comprises adding the first treated water stream, comprising a second organic material, from the anaerobic biodigester to an aerobic biodigester. Aerobic biodigestion conditions are implemented in the aerobic biodigester to convert the first treated water stream to a second treated water stream and a digestate solid. The second treated water stream is introduced to the thermal desalination unit and subsequently to the electrolysis unit as additional feed. Alternatively, in some embodiments, when the thermal desalination unit is not available, the second treated water stream can be discharged through the seawater outfall. Alternatively, in some embodiments, the anaerobic biodigester is intentionally or unintentionally shut down, such that the process wastewater stream, comprising the first organic material, is fed to the aerobic biodigester instead of the anaerobic biodigester, thus maintaining treatment capacity in a configuration without an anaerobic biodigester.

In some embodiments, an eFuels plant comprises an electrolysis unit and a hydrocarbon synthesis (HS) system. The electrolysis unit comprises one or more AECs and/or one or more PEMs. In some embodiments, the one or more AECs comprise one or more low pressure AECs, one or more high pressure AECs, or a combination thereof. In some embodiments, the one or more PEMs comprise one or more low pressure PEMs, one or more high pressure PEMs, or a combination thereof. As used in this context, "low pressure" means atmospheric pressure or less than or equal to 10 barg, and "high pressure" means greater than 10 barg, greater than or equal to 20 barg, greater than or equal to 30 barg, and/or less than or equal to 40 barg, less than or equal to 60 barg, less than or equal to 80 barg, and/or less than or equal to 100 barg. In the electrolysis unit, electricity and a water feed stream are reacted to form hydrogen and oxygen product streams. The HS system converts the carbon dioxide and hydrogen product streams to produce one or more of synthetic liquefied gas (SLG), a synthetic light distillate (SLD), a synthetic middle distillate (SMD), and a synthetic heavy distillate (SHD).

In some embodiments, an eFuels plant further comprises a hydrogen storage system (and optionally a hydrogen compression system), a carbon dioxide compression and storage system, a SLG compression and storage system, or a combination thereof.

In some embodiments, the system further comprises a direct air capture (DAC) unit to recover carbon dioxide from air to feed to the HS system.

In some embodiments, the system further comprises a thermal desalination unit and a water demineralization unit to produce the water feed stream to the electrolysis unit.

In some embodiments, the system further comprises an oxygen-fired heater (OFH) adapted for receiving combustion reactants in a combustion zone, producing heat, and emitting OFH flue gas, comprising carbon dioxide, as a combustion product. The combustion reactants comprise at least a portion of the oxygen from the electrolysis unit and a gas stream from the HS system. Piping, valves, heat exchangers, pumps, compressors, and the like are arranged to deliver the OFH flue gas, comprising carbon dioxide, feed to one or more process units in the HS system, such as a reverse water-gas shift reactor. In some embodiments, a portion of the OFH flue gas is recycled to the combustion zone of the OFH to control combustion temperature. The OFH further comprises a heating zone adapted for receiving at least one steam stream from the HS system, transferring heat from the combustion zone to convert the at least on steam stream to a superheated steam stream, and withdrawing the superheated steam stream for transmission to the HS system to provide heat for one or more process units in the HS system.

In some embodiments, the system further comprises a steam turbine generator to receive the superheated steam stream from the oxygen-fired heater to produce electricity and a steam condensate stream to be sent as additional feed to a demineralization unit.

In some embodiments, the system further comprises an anaerobic digester to receive a process wastewater stream from the HS system to produce a gas stream and a first treated water stream, wherein the gas stream is recycled to the HS system.

In some embodiments, the system further comprises an aerobic digester for receiving the first treated water stream and producing a second treated water stream to be sent as additional feed to a thermal desalination unit.

The above paragraphs present a summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWINGS

The claimed subject matter may be understood by reference to the following description taken in conjunction with the accompanying drawings, in which like reference numerals identify like elements, equipment to which reference is made is defined in the description, and in which:

Figure 1:
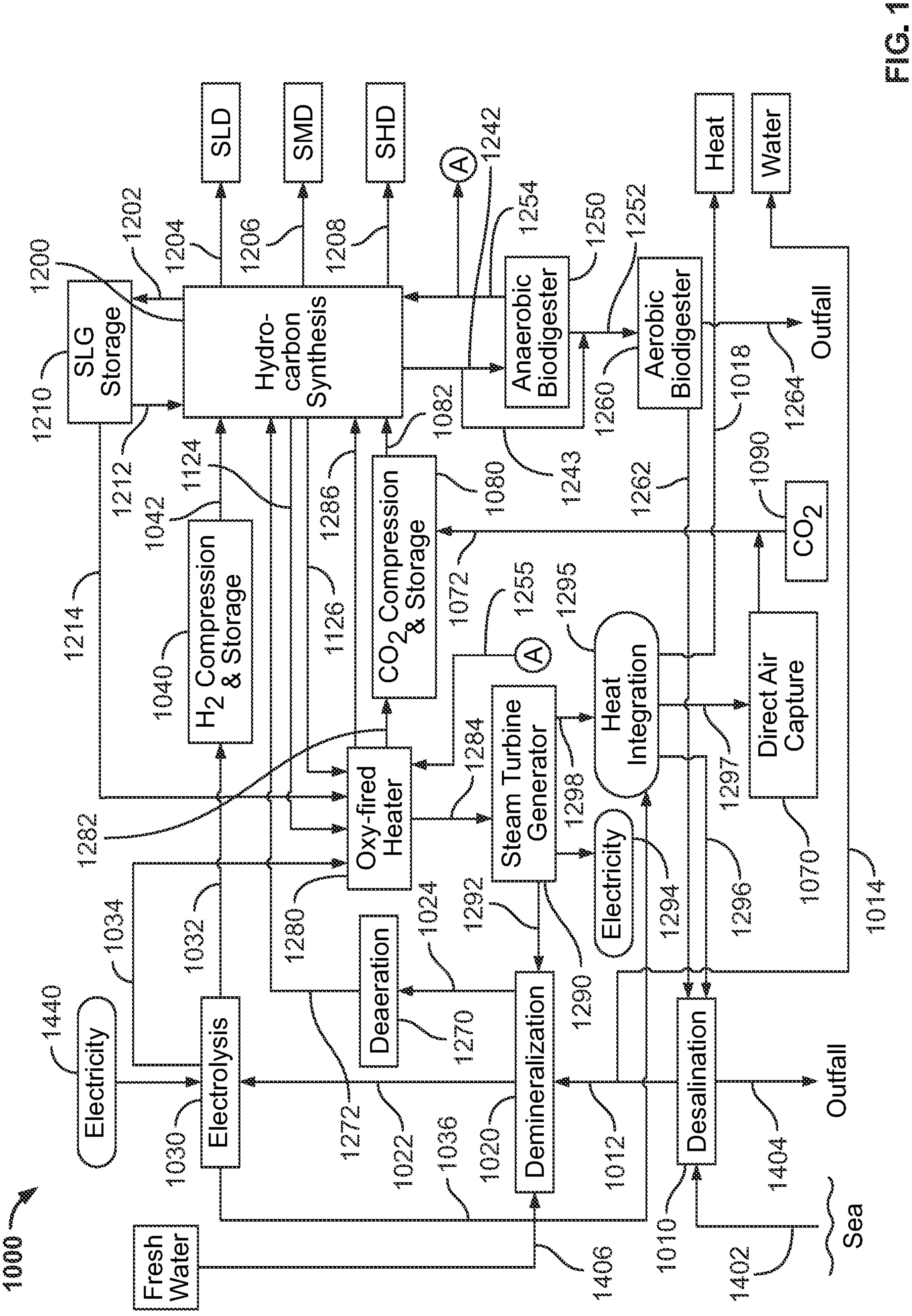
FIG. 1 is a block flow diagram of an exemplary eFuels plant for implementing normal operations of the process disclosed herein.

While the disclosed process and system are susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the subject matter claimed below will now be disclosed. In the interest of clarity, some features of some actual implementations may not be described in this specification. It will be appreciated that in the development of any such actual embodiments, numerous implementation-specific decisions must be made to achieve the developer's specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than the broadest meaning understood by skilled artisans, such a special or clarifying definition will be expressly set forth in the specification in a definitional manner that provides the special or clarifying definition for the term or phrase. It must also be noted that, as used in the specification and the appended claims, the singular forms "a," "an," and "the" include plural references unless otherwise specified.

For example, the following discussion contains a non-exhaustive list of definitions of several specific terms used in this disclosure (other terms may be defined or clarified in a definitional manner elsewhere herein). These definitions are intended to clarify the meanings of the terms used herein. It is believed that the terms are used in a manner consistent with their ordinary meaning, but the definitions are nonetheless specified here for clarity.

Definitions

As used herein, "eFuels," means synthetic hydrocarbon products produced as disclosed herein, including, but not limited to one or more of synthetic liquefied gas (SLG), a synthetic light distillate (SLD), a synthetic middle distillate (SMD), and a synthetic heavy distillate (SHD). eFuels are produced using electricity, carbon dioxide and water feed streams. In some embodiments, eFuels are produced using electricity generated without the use of a petroleum feedstock to the eFuels plant. In some embodiments, the carbon dioxide is derived without the use of petroleum feedstock. In some embodiments, the electricity originates from renewable sources.

As used herein, "petroleum," means crude oil or a fossil fuel, which is a liquid mixture of hydrocarbons present in certain rock strata that can be extracted and refined to produce fuels including gasoline, kerosene, and diesel oil.

As used herein, "synthetic heavy distillate (SHD)," means a synthetic hydrocarbon product produced as disclosed herein and not containing any molecules derived from petroleum. SHD consists of hydrocarbons having carbon numbers predominantly in the range of $C_{14}$ through $C_{20}$ and a boiling in the range of approximately 150° C. to 360° C. and is analogous to diesel produced from a petroleum feedstock.

As used herein, "synthetic light distillate (SLD)," means a synthetic hydrocarbon product produced as disclosed herein and not containing any molecules derived from petroleum. SLD consists of hydrocarbons having carbon numbers predominantly in the range of $C_5$ through $C_{10}$ and a boiling in the range of approximately 20° C. to 200° C. and is analogous to naphtha produced from a petroleum feedstock.

As used herein, “synthetic liquefied gas (SLG),” means a synthetic hydrocarbon product produced as disclosed herein and not containing any molecules derived from petroleum. SLG consists primarily of propane, butane, propylene, butylene, and isobutane and is analogous to liquefied petroleum gas (LPG) produced from a petroleum feedstock.

As used herein, “synthetic middle distillate (SMD),” means a synthetic hydrocarbon product produced as disclosed herein and not containing any molecules derived from petroleum. SMD consists of hydrocarbons having carbon numbers predominantly in the range of $C_{10}$ through $C_{16}$ and a boiling in the range of approximately 140° C. to 300° C. and is analogous to kerosene produced from a petroleum feedstock.

The following abbreviations are used herein:

| ABBREVIATION | TERM |
| --- | --- |
| AECs | Alkaline electrolysis cells |
| eFuels | Synthetic hydrocarbons produced as disclosed herein from non-petroleum feed sources and in some instances using electricity generated without the direct use of petroleum |
| LPG | Liquefied petroleum gas, comprising one or more of propane, propylene, butylene, isobutane, and n-butane, and produced from a petroleum feed source |
| PEMs | Proton exchange membrane cells |
| RFCER | Renewable feed and carbon/energy recovery system |
| RWGS | Reverse water gas shift reaction |
| SHD | Synthetic heavy distillate; analogous to diesel produced from a petroleum feed source |
| SLD | Synthetic light distillate; analogous to naphtha produced from a petroleum feed source |
| SLG | Synthetic liquefied gas; analogous to LPG produced from a petroleum feed source |
| SMD | Synthetic middle distillate; analogous to kerosene produced from a petroleum feed source |
| wt % | Weight percent |

It is noted that in this disclosure and particularly in the claims and/or paragraphs, terms such as “comprises”, “comprised”, “comprising” and the like can have the meaning attributed to it in U.S. patent law; e.g., they can mean “includes”, “included”, “including”, and the like; and that terms such as “consisting essentially of” and “consists essentially of” have the meaning ascribed to them in U.S. patent law, e.g., they allow for elements not explicitly recited, but exclude elements that are found in the prior art or that affect a basic or novel characteristic of the disclosure.

Hydrocarbon Synthesis System

The eFuels plant disclosed herein comprises a hydrocarbon synthesis (HS) system and a renewable feed and carbon/energy recovery (RFCER) system. In some embodiments, the HS system comprises a reverse water-gas shift (RWGS) reactor to convert hydrogen and carbon dioxide feed stream to syngas, comprising hydrogen and carbon monoxide. In some embodiments, syngas from the RWGS is fed to a Fischer-Tropsch (FT) reactor to produce FT hydrocarbon products, including one or more of FT wax, FT condensate, and FT tail gas. In some embodiments, FT tail gas is recycled as additional feed to the FT reactor and/or the RWGS reactor. In some embodiments, FT wax, FT condensate, and a portion of the hydrogen produced in the electrolysis unit are fed to a hydrocracking reactor to produce a hydrocarbon product. In some embodiments, the hydrocarbon product is then introduced to one or more distillation columns to separate the hydrocarbon product into one or more of a synthetic liquefied gas (SLG), a synthetic light distillate (SLD), a synthetic middle distillate (SMD), and a synthetic heavy distillate (SHD).

Syngas Production

In some embodiments, the process implemented in the HS system comprises introducing electricity and the hydrogen stream and carbon dioxide stream produced in the RFCER system to a reverse water-gas shift (RWGS) reactor under reaction conditions sufficient to produce a RWGS product stream comprising syngas. In some embodiments, syngas can be produced in a syngas production process, such as, but not limited to, through reforming (e.g., steam and/or autothermal) and/or (partial) gasification of suitable feedstocks including biogas, pipeline natural gas, and biomass. In some embodiments, gasification includes process using useful feedstock, including but not limited to biomass and biomass derived feedstocks.

In some embodiments, the electricity consumed in the RWGS reaction comprises electricity from the electrical power grid supporting the eFuels plant and/or electricity delivered from the RFCER system. In some embodiments, all or a majority of the power from the electrical grid is derived from renewable sources, such as, but not limited to, solar energy, wind energy, hydroelectric energy, geothermal energy, biomass combustion, nuclear energy, tidal energy, wave energy, hydrogen fuel cells, or a combination thereof. Further, in some embodiments, synthetic hydrocarbon fuels produced by the process disclosed herein are inventoried for on-premise generation of electricity to permit continued operation of the process disclosed herein in spite of fluctuations in power available from the electrical grid and/or the RFCER system. Maximizing renewable energy sources used to power water electrolysis results in minimizing the $CO_2$ footprint and/or carbon intensity attributable to hydrogen production since fossil fuels are not used or are used only minimally in its production.

Reaction conditions with respect to RWGS reactants include, but are not limited to, pressure, temperature, and composition of reactants.

Reaction conditions within the RWGS reactor include, but are not limited to, pressure, temperature, and specific energy consumption sufficient to produce a syngas product stream, comprising carbon monoxide and hydrogen in relative amounts and at conditions suitable for use as a feed stream to a FT process.

RWGS reactions and reactors useful in the process disclosed herein are described in more detail in U.S. Pub. App. Nos. 2018/0243711A1, 2020/0317514A1, 2021/0130965A1, 2021/0340015A1, and 2022/0410109A1; PCT Pub. Nos. WO 2022/112309A1 and WO 2022/253965A1; and *Ind. Eng. Chem. Res.* 2022, 61, 34, 12857-12865, Pub. Aug. 19, 2022, https://doi.org/10.1021/acs.iecr.2c00305, Copyright 2022 The Authors, published by American Chemical Society; Bown, R. M., Joyce, M., Zhang, Q., Reina, T. R. and Duyar, M. S. (2021), Identifying Commercial Opportunities for the Reverse Water Gas Shift Reaction. Energy Technol., 9: 2100554. https://doi.org/10.1002/ente.202100554; and Zhu, M., Ge, Q. & Zhu, X. Catalytic Reduction of $CO_2$ to CO via Reverse Water Gas Shift Reaction: Recent Advances in the Design of Active and Selective Supported Metal Catalysts. Trans. Tianjin Univ. 26, 172-187 (2020), https://doi.org/10.1007/s12209-020-

00246-8, all of which are fully incorporated by reference herein for all jurisdictions in which such incorporation is permitted.

Syngas Dispositions

The process disclosed herein is primarily directed to production of synthetic hydrocarbon products through reacting syngas in a FT reaction followed by hydrocracking of the FT product. Alternatively, syngas can be used as a source of hydrogen or as a fuel. Chemical uses include the production of methanol, which is a precursor to acetic acid and many acetates. Liquid fuels, waxes, fine chemicals, and lubricants can be derived from syngas via the FT process and previously by the Mobil methanol to gasoline process. Ammonia can be produced from syngas by the Haber process, which converts atmospheric nitrogen ($N_2$) into ammonia, which is used as a fertilizer. Syngas may further be converted to oxo alcohols via an intermediate aldehyde. Furthermore, the syngas produced is converted to methanol that is used in ExxonMobil's gas to olefins process.

Fischer-Tropsch Unit

In some embodiments, the process implemented in the HS system further comprises adding at least a portion of the syngas stream to a FT reactor under reaction conditions sufficient to form a FT tail gas stream, a FT condensate stream, and a FT wax stream, wherein the FT unit includes common equipment associated with FT reactors, such as heat exchangers, decanters, pumps, compressors, valves, reflux loops, and the like. The FT tail gas can be further processed and recycled as additional feed to the RWGS reactor or the FT reactor. The FT condensate stream, the FT wax stream, and hydrogen are optionally introduced as feed to a hydrocracking and/or (mild) hydroisomerization reactor.

Fischer-Tropsch technology, reactions and reactors useful in the process disclosed herein are described in more detail in U.S. Pub. No. 2022/0081292A1; U.S. Pat. Nos. 9,752,080, 8,889,746, 6,872,753, and 9,890,041; PCT Pub. Nos. WO 2023/064089A1. WO 2022/038230A1, WO 2023/060707A1, WO 2023/064150A1, WO 2022/053260A1, WO 2022/049148A1, WO 2021/180805A1, WO 2021/110754A1, WO 2022/171643A1, and WO 2022/079002A1; and Michela Martinelli, Muthu Kumaran Gnanamani, Steve LeViness, Gary Jacobs, Wilson D. Shafer, An overview of Fischer-Tropsch Synthesis: XtL processes, catalysts and reactors, *Applied Catalysis A: General*, Volume 608, 2020, 117740, ISSN 0926-860X, https://doi.org/10.1016/j.apcata.2020.117740; Marco Marchese, Emanuele Giglio, Massimo Santarelli, Andrea Lanzini, Energy performance of Power-to-Liquid applications integrating biogas upgrading, reverse water gas shift, solid oxide electrolysis and Fischer-Tropsch technologies, *Energy Conversion and Management*: X, Volume 6, 2020, 100041, ISSN 2590-1745, https://doi.org/10.1016/j.ecmx.2020.100041; Dieterich, Vincent and Buttler, Alexander and Hanel, Andreas and Spliethoff, Hartmut and Fendt, Sebastian, Power-to-liquid via synthesis of methanol, DME or Fischer-Tropsch-fuels: a review, *Energy Environ. Sci.,* 2020, vol. 13, issue 10, pp. 3207-3252, The Royal Society of Chemistry, http://dx.doi.org/10.1039/D0EE01187H, all of which are fully incorporated by reference herein for all jurisdictions in which such incorporation is permitted.

Hydrocracking Unit

In some embodiments, the process implemented in the HS system comprises adding a portion of the hydrogen stream produced in the electrolysis unit, the FT condensate, and the FT wax to a hydrocracking and/or (mild) hydroisomerization reactor under reaction conditions sufficient to produce a hydrocracking product comprising a synthetic hydrocarbon stream, wherein the hydrocracking unit includes common equipment associated with hydrocracking reactors, such as heat exchangers, decanters, pumps, compressors, valves, reflux loops, and the like.

Hydrocracking reactions and reactors useful in the process disclosed herein are described in more detail in U.S. Publication No. 202139562A1; U.S. Pat. Nos. 3,268.436, 4,618,412, 4,935.120, 5,378,348, 6,583,186, 10,487,273, and 11,485,918; PCT Pub. Nos. WO 2022/034181A1, WO 2021/204621A1, and WO 2023/001695A1; and Hydrocracking of Fischer-Tropsch Paraffin Mixtures over Strong Acid Bifunctional Catalysts to Engine Fuels, Tomasek, Lonyi, Valyon, Wollmann, & Hancsók, 2020 Oct. 20, 2020, doi: 10.1021/acsomega.0c02711, *ACS Omega,* 26413, 26420, vol. 5, issue 41, American Chemical Society, doi: 10.1021/acsomega.0c02711; Pleyer, O.; Vrtiška, D.; Straka, P.; Vráblík, A.; Jenčík, J.; Šimáček, P. Hydrocracking of a Heavy Vacuum Gas Oil with Fischer-Tropsch Wax. Energies 2020, 13, 5497, https://doi.org/10.3390/en13205497; and Pleyer, Olga & Petr, Straka & Vrtiška, Dan & Hájek, Jiří & Černý, Radek. (2020). Hydrocracking of Fischer-Tropsch Wax. Paliva. 26-33.10.35933/paliva.2020.02.01, all of which are fully incorporated by reference herein for all jurisdictions in which such incorporation is permitted.

Distillation

In some embodiments, the process implemented in the HS system further comprises feeding a synthetic hydrocarbon stream to one or more distillation columns to form one or more synthetic hydrocarbon products. The one or more distillation columns include common equipment associated with distillation columns, such as heat exchangers, decanters, pumps, compressors, valves, reflux loops, and the like.

Process Wastewater Treatment

Process wastewater is generated as a byproduct of the processes within the HS system, in particular the FT process. In some embodiments, the process implemented in the HS system further comprises treating process wastewater with a sour water stripper and a water degasifier.

In some embodiments, wastewater to be treated is fed to a sour water stripper. A sour wastewater feed stream is added to a sour water stripper, wherein the sour wastewater feed stream has a first content of hydrogen sulfide, a first content of ammonia, or a combination thereof. Stripping conditions are implemented in the sour water stripper. Products withdrawn from the sour water stripper comprise a sour gas stream and a stripped water stream. The sour gas comprises hydrogen sulfide, ammonia, or a combination thereof. The stripped water stream comprises a second content of hydrogen sulfide, a second content of ammonia, or a combination thereof. The second content of hydrogen sulfide is less than the first content of hydrogen sulfide, the second content of ammonia is less than the first content of ammonia, or a combination thereof.

Sour water stripping reactions and apparatuses useful in the process disclosed herein are described in more detail in U.S. Pat. Nos. 3,761,409, 4,076,621, 8,685,236, and 9,394,188; and Assessment of a Sour Water Treatment Unit Using Process Simulation, Parametric Sensitivity, and Exergy Analysis, Mestre-Escudero, R., Puerta-Arana, A., González-Delgado, Á., 2020 Sep. 22, 2020, *ACS Omega*, SP-23654, EP-23661, vol. 5, issue 37, American Chemical Society, doi: 10.1021/acsomega.0c02300; Umer Zahid, Techno-economic evaluation and design development of sour water stripping system in the refineries, Journal of Cleaner Production, Volume 236, 2019, 117633, ISSN 0959-6526, https://doi.org/10.1016/j.jclepro.2019.117633; Alvaro de Farias Soares, Eduardo Dellosso Penteado, Anthony Andrey Ramalho Diniz, Andrea Komesu, Influence of operational parameters in sour water stripping process in effluents treatment, *Journal of Water Process Engineering*, Volume 41, 2021, 102012, ISSN 2214-7144, https://doi.org/10.1016/j.jwpe.2021.102012, all of which are fully incorporated by reference herein for all jurisdictions in which such incorporation is permitted.

In some embodiments, process wastewater is further treated by feeding the stripped sour water to a water degasifier. The stripped sour water feed stream is added to a water degasifier, wherein the feed stream comprises a first content of oxygen, a first content of carbon dioxide, or a combination thereof. Degasifying conditions are implemented in the water degasifier. Products withdrawn from the water degasifier comprise a removed gas stream and a degassed water stream. The removed gas comprises oxygen, carbon dioxide, or a combination thereof. The degassed water stream comprises a second content of oxygen, a second content of carbon dioxide, or a combination thereof. The second content of oxygen is less than the first content of oxygen, the second content of carbon dioxide is less than the first content of carbon dioxide, or a combination thereof.

Water degasifying reactions and apparatuses useful in the process disclosed herein are described in more detail in U.S. Pat. Nos. 9,611,154 and 10,875,767; and Pon Saravanan, N., and Marlene J. Van Vuuren. "Process Wastewater Treatment and Management in Gas-to-Liquids Industries." Paper presented at the SPE Oil and Gas India Conference and Exhibition, Mumbai, India, January 2010. doi: https://doi.org/10.2118/126526-MS (https://onepetro.org/SPEOGIC/proceedings-abstract/10OGIC/All-10OGIC/109660), all of which are fully incorporated by reference herein for all jurisdictions in which such incorporation is permitted.

Renewable Feed and Carbon/Energy Recovery System

The eFuels plant disclosed herein comprises a hydrocarbon synthesis (HS) system and a renewable feed and carbon/energy recovery (RFCER) system. In some embodiments, the RFCER system comprises an electrolysis unit, one or more of a thermal desalination unit, a direct air capture unit, a hydrogen storage system (and optionally a hydrogen compression system), a carbon dioxide compression and storage system, an oxygen-fired heater, a steam turbine generator, a heat integration system, and anaerobic and/or aerobic biodigestion units.

Electrolysis Unit

Electricity and a water feed stream are introduced into the electrolysis unit under reaction conditions sufficient to form a hydrogen stream and an oxygen stream. In some embodiments, the electricity consumed in the electrolysis reaction comprises electricity from the electrical power grid supporting the eFuels plant and/or electricity delivered from the RFCER system. In some embodiments, all or a majority of the power from the electrical grid is derived from renewable sources, such as, but not limited to, solar energy, wind energy, hydroelectric energy, geothermal energy, biomass combustion, nuclear energy, tidal energy, wave energy, hydrogen fuel cells, or a combination thereof. Further, in some embodiments, synthetic hydrocarbon fuels produced by the process disclosed herein are inventoried for on-premise generation of electricity to permit continued operation of the process disclosed herein in spite of fluctuations in power available from the electrical grid and/or the RFCER system. In some embodiments, water electrolysis can be powered by renewable sources. Maximizing renewable energy sources used to power water electrolysis results in minimizing the $CO_2$ footprint and/or carbon intensity attributable to hydrogen production since fossil fuels are not used or are used only minimally in its production.

Water electrolysis is a process that uses electrical energy to split water molecules ($H_2O$) into hydrogen gas ($H_2$) and oxygen gas ($O_2$) through an electrochemical reaction. The overall chemical equation for water electrolysis is: $2H_2O \rightarrow 2H_2 + O_2$.

Water electrolysis typically involves the use of an electrolysis cell, which consists of two electrodes, an anode and a cathode, immersed in a water-based electrolyte solution. When an electric current is applied to the electrodes, the water molecules at the anode are oxidized to release oxygen gas and positively charged hydrogen ions (H+). At the cathode, the hydrogen ions and electrons (e−) combine to form hydrogen gas.

The anode and cathode are typically made of a conductive material, such as platinum or other metals that are resistant to corrosion and are separated by a membrane or diaphragm that prevents the gases from mixing.

The efficiency of water electrolysis depends on several factors, including the current density, the temperature and pressure of the electrolyte, and the quality of the electrodes and the membrane. High current density and low electrolyte temperature and pressure can increase the rate of reaction but may also lead to reduced efficiency and increased energy consumption. The use of high-quality electrodes and membranes can improve the efficiency and durability of the electrolysis cell.

In some embodiments, a hydrogen feed stream is provided by an electrolysis unit, comprising one or more alkaline electrolysis cells (AECs) and one or more proton exchange membrane cells (PEMs). Alkaline electrolysis is an electrochemical process for the production of hydrogen gas and oxygen gas from water using an alkaline electrolyte, typically a solution of potassium hydroxide (KOH) or sodium hydroxide (NaOH). In alkaline electrolysis, a voltage is applied across the anode and cathode, which are separated by a porous diaphragm or membrane to prevent mixing of the products. Proton exchange membrane (PEM) electrolysis is an electrochemical process for the production of hydrogen gas and oxygen gas from water. In PEM electrolysis, a voltage is applied across a proton exchange membrane, which separates the anode and cathode compartments of the electrolyzer. The electrolysis reaction occurs at the electrodes, where water is oxidized at the anode to form oxygen gas and hydrogen ions (protons), while the hydrogen ions are reduced at the cathode to form hydrogen gas.

In some embodiments, the one or more AECs comprise one or more low pressure AECs, one or more high-pressure AECs, or any combination thereof. In some embodiments, the one or more PEMs comprise one or more low pressure PEMs, one or more high-pressure PEMs, or any combination thereof. In some embodiments, the electrolysis unit comprises one or more low pressure AECs and one or more one or more low pressure PEMs or any combination thereof. In some embodiments, the electrolysis unit comprises one or more low pressure AECs, one or more high-pressure AECs, and one or more one or more high-pressure PEMs, or any combination thereof.

In some embodiments, the electrolysis unit comprises one or more high-pressure AECs and one or more one or more high-pressure PEMs, or any combination thereof. As used in this context, "low pressure" means atmospheric pressure or less than or equal to 10 barg, and "high pressure" means greater than or equal to 10 barg, greater than or equal to 20 barg, greater than or equal to 30 barg, and/or less than or equal to 40 barg, less than or equal to 60 barg, less than or equal to 80 barg, and/or less than or equal to 100 barg. In the electrolysis unit, electricity and a water feed stream are reacted to form hydrogen and oxygen product streams.

Alkaline Electrolysis Cells

Reaction conditions with respect to electrolysis reactants include, but are not limited to, pressure, temperature, and composition of reactants.

In some embodiments, water is fed to the electrolysis apparatus has one or more of: a) a temperature in the range of from 0° C. to 100° C., from 5° C. to 50° C., or from 10° C. to 35° C.; b) a pressure in the range of from 10 kPa to 10,000 kPa, from 50 kPa to 7,000 kPa, or from 100 kPa to 5,000 kPa; c) a water hardness, as measured by electrical conductively in microsiemens per centimeter, in the range of from 0.01 μS/cm to 10 μS/cm, from 0.02 μS/cm to 8 μS/cm, or from 0.05 μS/cm to 5 μS/cm; and a mineral content in the range of from 0.1 mg/L to 20 mg/L, from 1 mg/L to 15 mg/L, or from 2 mg/L to 10 mg/L.

Reaction conditions within the electrolysis apparatus include, but are not limited to, pressure, temperature, and specific energy consumption.

In some embodiments, reaction conditions in the electrolysis apparatus are one or more of: a) a temperature in the range of from 20° C. to 95° C., from 30° C. to 90° C., or from 40° C. to 80° C.; b) a pressure in the range of from atmospheric pressure or less than or equal to 10 barg to 20 barg, 30 barg, 40 barg, 60 barg, 80 barg, or 100 barg; and c) a specific energy consumption in the range of from 3.0 $kWh/Nm^3$ to 6.0 $kWh/Nm^3$, from 3.2 $kWh/Nm^3$ to 5.5 $kWh/Nm^3$, or from 3.5 $kWh/Nm^3$ to 5.3 $kWh/Nm^3$.

In some embodiments, an anode catalyst is selected from one or more of Group 8 to 10 transition metals or from nickel, cobalt, and iron, and cathode catalyst is selected from one or more of Group 4 transition metals or from titanium, nickel, and zirconium.

Reaction conditions with respect to electrolysis products include, but are not limited to, pressure, temperature, and composition of products.

In some embodiments, hydrogen withdrawn from the electrolysis apparatus has one or more of: a) a temperature in the range of from 20° C. to 160° C., from 30° C. to 140° C., or from 40° C. to 120° C.; b) a pressure in the range of from atmospheric pressure or less than or equal to 10 barg to 20 barg, 30 barg, 40 barg, 60 barg, 80 barg, or 100 barg; and c) impurities less than 1.5 wt %, or in the range of from 0.03 wt % to 1.2 wt %, or from 0.05 wt % to 1 wt %.

In some embodiments, oxygen withdrawn from the electrolysis apparatus has one or more of: a) a temperature in the range of from 20° C. to 160° C., from 30° C. to 140° C., or from 40° C. to 120° C.; b) a pressure in the range of from atmospheric pressure or less than or equal to 10 barg to 20 barg, 30 barg, 40 barg, 60 barg, 80 barg, or 100 barg; and c) impurities less than 1.5 wt %, or in the range of from 0.03 wt % to 1.2 wt %, or from 0.05 wt % to 1 wt %.

Alkaline water electrolysis apparatuses useful in the process disclosed herein are described in more detail in U.S. Pub. Nos. 2023/0131407A1, 2023/0096320A1, 2022/0333260A1, 2022/0325425A1, 2022/0325424A1, and 2021/0115573A1; WO 2021/229963A1, WO 2022/258394A1, WO 2022/243441A1, and WO 2022/200315A1; and (Brochure) Nel Hydrogen Electrolysers, The World's Most Efficient and Reliable Electrolysers, copyright 2021 Nel ASA, PD-0600-0125 Rev D, https://nelhydrogen.com/wp-content/uploads/2020/03/Electrolysers-Brochure-Rev-D.pdf; (Brochure) Large-scale water electrolysis for green hydrogen production, Copyright thyssenkrupp nucera AG & Co. KGaA, https://thyssenkrupp-nucera.com/wp-content/uploads/2022/11/thyssenkrupp-nucera-green-hydrogen-solutions-brochure.pdf; (Brochure) Plug EX-4250D Electrolyzer (English), Published Date Apr. 20, 2022, https://resources.plugpower.com/electrolyzers/ex-4250d-f041122; (Brochure) DQ1000 Alkaline Electrolyser, DQ1000 @John Cockerill Renewables, hydrogen@johncockerill.com, h2.johncockerill.com https://h2.johncockerill.com/wp-content/uploads/2022/02/DQ-1000-def-2-HD.pdf; all of which are fully incorporated by reference herein for all jurisdictions in which such incorporation is permitted.

Proton Exchange Membrane Cells

Proton exchange membrane (PEM) electrolysis is an electrochemical process for the production of hydrogen gas and oxygen gas from water. In PEM electrolysis, a voltage is applied across a proton exchange membrane, which separates the anode and cathode compartments of the electrolyzer. The electrolysis reaction occurs at the electrodes, where water is oxidized at the anode to form oxygen gas and hydrogen ions (protons), while the hydrogen ions are reduced at the cathode to form hydrogen gas.

The efficiency of PEM electrolysis is dependent on several process conditions, including, but not limited to current density, electrolyte concentration, temperature, and pressure. The rate of hydrogen production is directly proportional to the current density applied in the cell. However, higher current densities lead to increased energy consumption. The rate of reaction increases with temperature due to increased kinetic energy of the reactant molecules. However, higher temperatures also increase the potential for degradation of the membrane and catalysts. Higher pressures can increase the solubility of hydrogen and oxygen gases in the electrolyte and reduce the energy required for gas compression. However, high-pressures also increase the cost and complexity of the system. Overall, PEM electrolysis is an attractive method for hydrogen production due to its high efficiency, fast response time (e.g., in the range of from 0.25 to 1 second per percent electrolyzer electrical load), and low environmental impact.

Reaction conditions with respect to electrolysis reactants include, but are not limited to, pressure, temperature, and composition of reactants.

In some embodiments, water is fed to the electrolysis apparatus has one or more of: a) a temperature in the range of from 0° C. to 100° C., from 5° C. to 50° C., or from 10° C. to 35° C.; b) a pressure in the range of from atmospheric pressure or less than or equal to 10 barg to 20 barg, 30 barg, 40 barg, 60 barg, 80 barg, or 100 barg; and c) a water hardness, as measured by electrical conductively in microsiemens per centimeter, in the range of from 0.01 μS/cm to 10 μS/cm, from 0.02 μS/cm to 8 μS/cm, or from 0.05 μS/cm to 5 μS/cm; and a mineral content in the range of from 0.1 mg/L to 20 mg/L, from 1 mg/L to 15 mg/L, or from 2 mg/L to 10 mg/L.

Reaction conditions within the electrolysis apparatus include, but are not limited to, pressure, temperature, and specific energy consumption.

In some embodiments, reaction conditions in the electrolysis apparatus are one or more of: a) a temperature in the range of from 20° C. to 95° C., from 30° C. to 90° C., or from 40° C. to 80° C.; b) a pressure in the range of from atmospheric pressure or less than or equal to 10 barg to 20 barg, 30 barg, 40 barg, 60 barg, 80 barg, or 100 barg; and c) a specific energy consumption in the range of from 3.0 $kWh/Nm^3$ to 6.0 $kWh/Nm^3$, from 3.2 $kWh/Nm^3$ to 5.5 $kWh/Nm^3$, or from 3.5 $kWh/Nm^3$ to 5.3 $kWh/Nm^3$.

In some embodiments, anode catalyst is selected from one or more of Group 13 post-transition metals or indium, and cathode catalyst is selected from one or more of Group 10 transition metals or platinum.

Reaction conditions with respect to electrolysis products include, but are not limited to, pressure, temperature, and composition of products.

In some embodiments, hydrogen withdrawn from the electrolysis apparatus has one or more of: a) a temperature in the range of from 20° C. to 160° C., from 30° C. to 140° C., or from 40° C. to 120° C.; b) a pressure in the range of from atmospheric pressure or less than or equal to 10 barg to 20 barg, 30 barg, 40 barg, 60 barg, 80 barg, or 100 barg; and c) impurities less than 1.5 wt %, or in the range of from 0.03 wt % to 1.2 wt %, or from 0.05 wt % to 1 wt %.

In some embodiments, oxygen withdrawn from the electrolysis apparatus has one or more of: a) a temperature in the range of from 20° C. to 160° C., from 30° C. to 140° C., or from 40° C. to 120° C.; b) a pressure in the range of from atmospheric pressure or less than or equal to 10 barg to 20 barg, 30 barg, 40 barg, 60 barg, 80 barg, or 100 barg; and c) impurities less than 1.5 wt %, or in the range of from 0.03 wt % to 1.2 wt %, or from 0.05 wt % to 1 wt %.

Proton exchange membrane electrolysis apparatuses useful in the process disclosed herein are described in more detail in U.S. Pat. No. 10,053,788; U.S. Pub. Nos. 2016/0089658A1, 2013/0092549A1, 2008/0118807A1, 2008/0026276A1, 2004/0214065A1, and 2004/0013925A1; PCT Pub. Nos. WO 2022/243441A1, and WO 2022/200315A1; and (Brochure) Nel Hydrogen Electrolysers, The World's Most Efficient and Reliable Electrolysers, copyright 2021 Nel ASA, PD-0600-0125 Rev D, https://nelhydrogen.com/wp-content/uploads/2020/03/Electrolysers-Brochure-Rev-D.pdf; [non-patent literature], all of which are fully incorporated by reference herein for all jurisdictions in which such incorporation is permitted.

Hydrogen Compression

In some embodiments, hydrogen from the electrolysis unit is produced at a pressure less than the pressure required for hydrogen feed to the HS system. Such embodiments additionally comprise a hydrogen compression system. Such hydrogen compression systems comprise one or more hydrogen compressors and ancillary equipment are well known to those skilled in the art and can be designed to impart a pressure increase to any or all hydrogen produced from the electrolysis unit as needed to be compatible with HS system feed requirements.

Discharge from the hydrogen compression system can be fed directly to the HS system, to pressurized hydrogen storage (wherein hydrogen is maintained at or about the discharge pressure of the hydrogen compression system), or a combination thereof. In some embodiments, hydrogen produced from the electrolysis unit can be stored at the pressure as produced, wherein hydrogen is withdrawn from such storage is routed to the hydrogen compression system prior to being fed to the HS system.

Hydrogen Storage

In some embodiments, the process for producing one or more synthetic hydrocarbon products further comprises sending hydrogen produced in the electrolysis apparatus to a hydrogen storage system. Such storage provides for optimization of electrical costs and/or stabilization of eFuels plant operations, and/or control of the process with fluctuating supply of electricity.

In some embodiments, overall reduction of electrical costs is achieved by use of stored hydrogen to allow intentional reduction in hydrogen production by reducing, idling, or shutting down all or a portion of the electrolysis unit. Electrical grids often have different costs in terms of monetary units per kilowatt-hour (mu/kWh). The cost of electricity in a green electrical grid can vary depending on several factors, including the availability of renewable energy sources, the demand for electricity, and the cost of operating and maintaining the grid infrastructure. Green electrical grids rely on renewable energy sources such as solar, wind, hydro, and geothermal power to generate electricity. These sources of energy are dependent on the weather and the availability of natural resources, which can cause fluctuations in the electricity supply and, therefore, the cost of electricity. For example, if there is a high demand for electricity on a sunny day, when solar power is abundant, the cost of electricity may be lower due to the abundance of supply. However, if there is low demand for electricity during periods of high wind or solar power generation, the availability and cost of electricity may be higher as renewable energy sources may be curtailed or excess power may need to be stored. In addition, the cost of electricity in a green electrical grid may also vary depending on the cost of maintaining and upgrading the grid infrastructure to accommodate the integration of renewable energy sources. This can include upgrading transmission lines and distribution networks to ensure reliable and efficient power delivery.

In some embodiments, stored hydrogen can be intentionally used to supplement or replace direct production of hydrogen from the electrolysis unit during time periods when costs of electricity from the grid are higher. Conversely, when the availability is high and costs of electricity from the grid are lower, the electrolysis unit can produce hydrogen in excess of the amount required for operation and the eFuels plant in order to build an inventory of high-pressure hydrogen in storage for use during a future time period of lower electricity availability from the grid. An availability and/or cost optimized cycle of higher, lower, and intermediate hydrogen production rates from the electrolysis unit in a specific eFuels plant is determined by parameters related to such eFuels plant, such as, but not limited to the availability and cost structure of the grid supplying electricity to such eFuels plant, the hydrogen storage capacity of such eFuels plant, and the desired production rate of eFuels products from the eFuels plant during a particular time period. In some embodiments, the eFuels plant further comprises a control system to assist the operator in balancing the timing and/or production rates and disposition of hydrogen produced by the electrolysis unit and timing and/or withdrawal rates of hydrogen withdrawn from the hydrogen storage system over a selected time period. Such a control system can assist the operator in minimizing the disruptions to operations and/or electrical costs of operation of the electrolysis unit and/or the eFuels plant on an hourly basis, a daily basis, a monthly basis, a yearly basis, or a combination thereof.

In some embodiments, timing and/or withdrawal rates of hydrogen from the storage system are determined by fluctuations in the amount of or outages of electricity available to be supplied to the eFuels plant from the grid. The inventory of high-pressure hydrogen in the hydrogen storage system provides an instantaneous response to unplanned reductions in hydrogen production rates from the electrolysis unit caused by an unplanned reduction in electricity supplied for the eFuels plant from the grid. This instantaneous withdrawal of hydrogen from the hydrogen storage system serves to offset the instantaneous loss of hydrogen production from the electrolysis unit and thereby stabilize the supply of hydrogen to the downstream units in the eFuels plant which are hydrogen consumers. This minimizes perturbations of operation of the eFuels plant in spite of fluctuations in the amount of electricity available for the eFuels plant from the grid.

Hydrogen can be stored physically as either a gas or a liquid. Storage of hydrogen as a gas typically requires high-pressure tanks (200 to 700 barg tank pressure). Storage of hydrogen as a liquid requires cryogenic temperatures because the boiling point of hydrogen at one atmosphere pressure is −252.8° C. In some embodiments, hydrogen is stored at conditions comprising one or more of: a) a temperature in the range of from 0° C. to 150° C., from 30° C. to 120° C., or from 40° C. to 100° C.; and b) a pressure in the range of from 2,000 kPa to 65,000 kPa, from 2,500 kPa to 45,000 kPa, or from 3,000 kPa to 35,000 kPa.

In some embodiments, hydrogen is stored in the form of a metal hydride, such as disclosed in more detail in U.S. Pub. Nos. 2019/0359483A1, 20200270126A1, and 2019/0359483A1; Gkanas, E. I.; Wang, C.; Shepherd, S.; Curnick, O. Metal-Hydride-Based Hydrogen Storage as Potential Heat Source for the Cold Start of PEM FC in Hydrogen-Powered Coaches: A Comparative Study of Various Materials and Thermal Management Techniques. *Hydrogen* 2022, 3, 418-432. https://doi.org/10.3390/hydrogen3040026; K. Malleswararao, Pradip Dutta, Srinivasa Murthy S, Applications of metal hydride based thermal systems: A review, Applied Thermal Engineering, Volume 215, 2022, 118816, ISSN 1359-4311, https://doi.org/10.1016/j.applthermaleng.2022.118816, (https://www.sciencedirect.com/science/article/pii/S1359431122007578); and https://www.gknhydrogen.com/technology/, the substance of which is fully incorporated by reference herein for all jurisdictions in which such incorporation is permitted. A metal hydride storage system typically requires moderate temperature and pressure conditions (e.g., from 0° C. to 80° C., from 0 barg to 50 barg).

Considerations for implementation of hydrogen storage can be found in (1) US Dept. of Energy, Office of Energy Efficiency & Renewable Energy, Hydrogen Storage, Hydrogen and Fuel Cell Technologies Office, https://www.energy.gov/eere/fuelcells/hydrogen-storage#:~:text=Hydrogen%20can%20be%20stored%20physically,pressure%20is%20%E2%88%92252.8%C2%B0C, and (2) International Energy Agency, Hydrogen Implementing Agreement, Hydrogen Production and Storage, R&D Priorities and Gaps, IEA Publications, 9, rue de la Fédération, 75739 Paris Cedex 15, printed in France by Stedi Média, January 2006, https://www.iea.org/reports/hydrogen-production-and-storage, both of which are fully incorporated by reference herein for all jurisdictions in which such incorporation is permitted.

Carbon Dioxide Feed

In some embodiments, the process implemented in the eFuels plant further comprises obtaining the first carbon dioxide stream as a feed stream to the RWGS reactor. Carbon dioxide feed can be supplied by one or more of: a) importing carbon dioxide from a source external to the process; b) feeding air to a direct air capture (DAC) unit to recover carbon dioxide; and c) combusting biomass or biogas to recover carbon dioxide. In some embodiments, imported $CO_2$ can be petroleum-derived, biogenic, or a combination thereof. Biogenic $CO_2$ relates to carbon in wood, paper, grass trimmings, and other biofuels that was originally removed from the atmosphere by photosynthesis and, under natural conditions, would eventually cycle back to the atmosphere as $CO_2$ due to degradation processes. Use of biogenic $CO_2$, $CO_2$ extracted from the atmosphere, and/or other $CO_2$ sources unrelated to fossil fuels result in synthetic hydrocarbon products (SLG, SLD, SMD, and SHD) that have a unique quality in terms of radioactive carbon dating, different from hydrocarbon products derived from fossil fuel feedstocks and/or $CO_2$ derived from fossil fuel or petroleum sources.

In some embodiments, at least a portion of the electricity consumed in the DAC reaction is derived from solar sources, wind sources, or a combination thereof from the electrical grid. Further, in some embodiments, synthetic hydrocarbon fuels produced by the process disclosed herein are inventoried for on-premise generation to electricity to permit continued operation of the process disclosed herein in spite of fluctuations in power available from the electrical grid.

In some embodiments, the carbon dioxide feed stream to the RWGS reactor has one or more of: a) a temperature in the range of from −60° C. to 200° C., from 0° C. to 120° C., or from 5° C. to 100° C.; b) a pressure in the range of from 100 kPa to 10,000 kPa, from 500 kPa to 7,000 kPa, or from 700 kPa to 5,000 kPa; and c) a content of gases other than carbon dioxide of less than 6 wt %, or in the range of from 0.1 wt % to 5 wt %, or from 0.05 wt % to 4 wt %.

In some embodiments, the process implemented in the eFuels plant further comprises recovering carbon dioxide from ambient air by means of a direct air capture (DAC) unit.

DAC reactions and apparatuses useful in the process disclosed herein are described in more detail in U.S. Pat. Nos. 11,623,863 and 11,560,343; PCT Pub. Nos. WO 2021/168498A1, WO 2021/253010A1, WO 2023/049952A1, WO 2023/056011A1, WO 2021/239748A1, WO 2021/156457A1, and WO 2023/043843A1; and (Brochure) Climeworks, Direct air capture: our technology to capture $CO_2$, https://climeworks.com/direct-air-capture; (Brochure) Carbon Engineering, Our Technology, Carbon Engineering Ltd., Copyright 2023, https://carbonengineering.com/our-technology/; (Brochure) Global Thermostat, A carbon negative solution, https://globalthermostat.com/; (Brochure) Mosaic Materials, Our Technology, https://mosaicmaterials.com/technology/; all of which are fully incorporated by reference herein for all jurisdictions in which such incorporation is permitted.

Carbon Dioxide Storage

In some embodiments, the process for producing one or more synthetic hydrocarbon products further comprises sending carbon dioxide produced by one or more of the direct air capture (DAC) unit and/or other carbon dioxide sources utilized in a specific eFuels plant to a carbon dioxide storage system. Such storage provides for optimization of electrical costs and/or stabilization of eFuels plant operations.

In some embodiments, overall reduction of electrical costs is achieved by use of stored carbon dioxide to allow intentional reduction in carbon dioxide production by reducing, idling, or shutting down all or a portion of the DAC unit and/or other carbon dioxide sources utilized in a specific eFuels plant. Electrical grids often have different costs in terms of monetary units per kilowatt-hour (mu/kWh). The cost of electricity in a green electrical grid can vary depending on several factors, including the availability of renewable energy sources, the demand for electricity, and the cost of operating and maintaining the grid infrastructure. Green electrical grids rely on renewable energy sources such as solar, wind, hydro, and geothermal power to generate electricity. These sources of energy are dependent on the weather and the availability of natural resources, which can cause fluctuations in the electricity supply and, therefore, the cost of electricity, the same as those discussed above for managing hydrogen supply.

In some embodiments, stored carbon dioxide can be intentionally used to supplement or replace direct production of carbon dioxide from the DAC unit and/or other carbon dioxide sources utilized in a specific eFuels plant during time periods. Conversely, when power supply from the grid is readily available, the DAC unit and/or other carbon dioxide sources utilized in a specific eFuels plant can produce carbon dioxide in excess of the amount required for operation and the eFuels plant in order to build an inventory of high-pressure carbon dioxide in storage for use during a future time period. Availability and cost optimized cycle of higher, lower, and intermediate carbon dioxide production rates from the DAC unit and/or other carbon dioxide sources utilized in a specific eFuels plant is determined by parameters related to such eFuels plant, such as, but not limited to the cost structure of the grid supplying electricity to such eFuels plant, the carbon dioxide storage capacity of such eFuels plant, and the desired production rate of eFuels products from the eFuels plant during a particular time period. In some embodiments, the eFuels plant further comprises a control system to assist the operator in balancing the timing and/or production rates and disposition of carbon dioxide produced by the DAC unit or other carbon dioxide sources utilized in a specific eFuels plant and timing and/or withdrawal rates of carbon dioxide withdrawn from the carbon dioxide storage system over a selected time period. Such control system can assist the operator in minimizing the electrical costs of operation of the DAC unit or other carbon dioxide sources utilized in a specific eFuels plant and/or the eFuels plant on an hourly basis, a daily basis, a monthly basis, a yearly basis, or a combination thereof.

In some embodiments, timing and/or withdrawal rates of carbon dioxide from the storage system are determined by fluctuations in the amount of or outages of electricity available to be supplied to the eFuels plant from the grid. The inventory of high-pressure carbon dioxide in the carbon dioxide storage system provides an instantaneous response to unplanned reductions in carbon dioxide production rates from the DAC unit or other carbon dioxide sources utilized in a specific eFuels plant caused by an unplanned reduction in electricity supplied for the eFuels plant from the grid. This instantaneous withdrawal of carbon dioxide from the carbon dioxide storage system serves to offset the instantaneous loss of carbon dioxide production from the DAC unit and/or other carbon dioxide sources utilized in a specific eFuels plant and thereby stabilize the supply of carbon dioxide to the downstream units in the eFuels plant which are carbon dioxide consumers. This minimizes perturbations of operation of the eFuels plant in spite of fluctuations in the amount of electricity or $CO_2$ available for the eFuels plant.

In some embodiments, the required changes to HS system operation triggered by intentional or unintentional changes in the DAC unit carbon dioxide production rates are mitigated or eliminated by decoupling the HS system from direct dependence on DAC production rates through the use of carbon dioxide storage.

In some embodiments, carbon dioxide is stored at conditions comprising one or more of: a) a temperature in the range of from −5° C. to −60° C., from −10° C. to −40° C., or from −15° C. to −35° C.; and b) a pressure in the range of from 600 kPa to 40,000 kPa, from 1,000 kPa to 3,000 kPa, or from 1,200 kPa to 2,500 kPa.

In some embodiments, the process implemented in the eFuels plant further comprises sending carbon dioxide produced to storage. Considerations for implementation of carbon dioxide storage can be found in (1) Linde, Safety advice, Carbon Dioxide, https://www.linde-gas.com/en/images/LMB_Safety%20Advice_01_66881_tcm17-165650.pdf, and (2) Pentair, Liquid CO2 Storage Tanks, https://foodandbeverage.pentair.com/en/products/pentair-liquid-co2-storage-tanks, both of which are fully incorporated by reference herein for all jurisdictions in which such incorporation is permitted.

Synthetic Liquefied Gas Storage

In some embodiments, stored SLG can be used to supplement feed to processing units in the HS system and/or as an additional or alternative fuel to the combustion zone of the oxygen-fired heater. Additional heat value and/or volume of SLG transfers additional heat to the heating zone of the oxygen-fired heater, which is translated to additional electricity from the steam turbine generator. In some embodiments, SLG fed to the HS system replaces direct production of hydrogen from the electrolysis apparatus. The reduced electrical consumption from reducing or shutting down hydrogen production from the electrolysis apparatus would permit continued operation of the process disclosed herein in spite of fluctuations in power available from the electrical grid.

In some embodiments, SLG is stored at conditions comprising one or more of: a) a temperature in the range of from −40° C. to 60° C., from −30° C. to 50° C., or from −20° C. to 40° C.; and b) a pressure in the range of from 500 kPa to 3,500 kPa, from 750 kPa to 2,500 kPa, or from 1,000 kPa to 2,000 kPa.

In some embodiments, the process implemented in the eFuels plant further comprises sending SLG produced in the HS system to storage. Considerations for implementation of SLG storage can be found in EuroTanks, LPG Storage, https://www.eurotanks.eu/lpg-storage-tank/, which is fully incorporated by reference herein for all jurisdictions in which such incorporation is permitted.

Back-up Electricity

In some embodiments, the eFuels plant further comprises facilities to supply a back-up source of electrical power to provide an uninterrupted power supply and mitigate power outages to the eFuels plant. The commercially viable range of electrical back-up capacities for one or more process units in the RFCER system or the eFuels plant can range from a few hundred kilowatt-hours to several hundred megawatt-hours, depending on the specific needs of the facility. In some embodiments, a back-up electrical power source comprises energy storage in an array of batteries, energy production from a stack of fuel cells, or a combination thereof.

In some embodiments, one or more grid-scale battery arrays have sufficient electrical storage to temporarily run one or more process units in the RFCER system or the eFuels plant. In some embodiments, the electrical power storage facility comprises grid-scale arrays of lead-acid batteries, lithium-ion batteries, flow batteries, or a combination thereof. These types of batteries are designed to deliver high energy output over an extended period, making them suitable for industrial applications that require a significant amount of power. Lead-acid batteries are the most commonly used type of battery in industrial applications due to their low cost and high reliability. They are suitable for short-duration applications, such as backup power during an outage. Lithium-ion Batteries have a higher energy density and longer cycle life than lead-acid batteries, making them suitable for longer-duration applications. They are more expensive than lead-acid batteries but offer better performance. Flow Batteries use chemical reactions to store and release energy, making them suitable for long-duration applications. They have a longer cycle life than lithium-ion batteries and can store energy for extended periods.

In some embodiments, grid-scale batteries are arranged in banks or arrays to provide the necessary electrical storage capacity. The arrangement of the batteries will depend on the specific requirements of the one or more process units being powered and the desired time for which the one or more process unit is to be powered by the battery array. The batteries will be connected in series or parallel configurations to increase voltage or current output, respectively.

In some embodiments, one or more grid-scale fuel cell stacks have sufficient electrical storage to temporarily run one or more process units in the RFCER system. Fuel cells are devices that convert the chemical energy of a fuel into electrical energy through an electrochemical process. In some embodiments, the fuel cells are powered by hydrogen, such as from the hydrogen storage system, and/or seawater, as disclosed in Chinese pat. no. CN218919069U. Each fuel cell stack consists of individual fuel cells connected in series or parallel configurations, depending on the required output voltage and current. The fuel cells themselves are typically made up of a membrane electrode assembly (MEA), which includes an electrolyte membrane, catalyst layers, and gas diffusion layers.

In some embodiments, a battery array further comprises a battery management system (BMS) to ensure that the batteries are operating efficiently and to protect them from damage. The BMS monitors the battery's state of charge, temperature, and other factors to optimize its performance and prevent overcharging or over-discharging. Like batteries, fuel cells also require a management system to ensure optimal performance and prevent damage. This may include a control system to manage the fuel flow and voltage output, as well as monitoring systems to measure the temperature and pressure of the fuel cell stack.

The specific arrangement of batteries and/or fuel cells in the RFCER system or the eFuels plant would depend on a variety of factors, including the specific requirements of the process unit being powered and the available space for the battery system. Typically, large-scale battery systems are designed with a series of modules, each containing multiple individual battery cells, that can be configured in a variety of ways to meet the specific needs of the application. The modules can then be linked together to create a larger battery array that can provide the necessary electrical storage and power output. Large-scale fuel cell systems typically consist of multiple individual fuel cells that can be connected in series or parallel to provide the necessary power output. The fuel cells themselves are often arranged in stacks, with each stack containing multiple individual cells connected in series. Multiple stacks can then be connected in parallel to create a larger fuel cell array. The batteries systems and/or the fuel cell systems may also be coupled with inverters, transformers, and other equipment to ensure that the electrical output is compatible with the needs of the one or more process units being powered.

There are several manufacturers of large-scale batteries that could potentially provide enough electrical storage to temporarily run a process unit in a refinery. Some of the most prominent manufacturers in this space include Tesla, LG Chem, Samsung SDI, and BYD. Unlike batteries, which store electrical energy chemically, fuel cells generate electricity through a chemical reaction between hydrogen and oxygen. There are several manufacturers of large-scale fuel cells, including Ballard Power Systems, Bloom Energy, and FuelCell Energy.

Seawater Processing

In some embodiments, the process implemented in the eFuels plant further comprises adding sea water to a desalinization unit and withdrawing a first treated water effluent to produce the first water stream, and optionally feeding at least a portion of the first treated water effluent to a demineralization unit and withdrawing a second treated water effluent to produce the first water stream.

In some embodiments, cooling of the RWGS product stream for recovery of the syngas is implemented in a first heat exchanger wherein a cooling medium comprises the first treated water effluent, the second treated water effluent, or a combination thereof. The cooling medium is converted to a first high-pressure steam stream.

The thermal desalination unit can run in at least two extreme modes of operation, the overall efficiency of the integrated process depends on whether there is an option for export of low-grade heat or an option for export of potable water from the RFCER system.

In some embodiments, low-grade heat export from the RFCER system is available. The thermal desalination distillate production is reduced to balance the water requirements and low grade heat balance. While operating in low distillate extraction mode, the seawater return quality has low salinity increased compared to the maximum distillate operating mode.

In some embodiments, low-grade heat export is not available. All low-grade heat from the electrolysis unit and HS are utilized within the thermal desalination unit, and surplus potable water for export is produced. As the salinity of the seawater return will be higher than generally allowed for discharge to sea in some jurisdictions, a salt crystallization unit be added to treat the effluent from the thermal desalinization unit to produce clean water for export from the RFCER system with zero liquid discharge to the sea.

Desalination technology and apparatuses useful in the process disclosed herein are described in more detail in U.S. Pub. Nos. 2008/0277344A1, 2012/0234664A1, and 2010/0072136A1; U.S. Pat. Nos. 6,783,682, 8,696,908, and 9,126,149; and Commercial Thermal Technologies for Desalination of Water from Renewable Energies: A State of the Art Review, https://www.mdpi.com/2227-9717/9/2/262; Thermodynamic, Exergy, and Thermoeconomic analysis of Multiple Effect Distillation Processes, https://www.sciencedirect.com/science/article/pii/B978012815244700012X; and Energy consumption and water production cost of conventional and renewable-energy-powered desalination processes, https://www.sciencedirect.com/science/article/abs/pii/S1364032113000208; Entropie-Veolia Technologies, https://www.entropie.com/solutions/technologies; all of which are fully incorporated by reference herein for all jurisdictions in which such incorporation is permitted.

Demineralization processes and apparatuses useful in the process disclosed herein are described in more detail in U.S. Pub. No. 2006/0243647; U.S. Pat. Nos. 3,425,937, 3,444,079, 3,658,674, 4,648,976, 4,820,421, and 5,468,395; and [non-patent literature], all of which are fully incorporated by reference herein for all jurisdictions in which such incorporation is permitted.

Oxygen-Fired Heater

In some embodiments, the process implemented in the eFuels plant further comprises adding at least a portion of the oxygen stream produced from the electrolysis apparatus and a fuel gas stream comprising one or more of HS system purge gas, HS system off gas, and SLG withdrawn from the HS system and/or the SLG storage system as fuel to an oxygen-fired heater. a second carbon dioxide stream is recovered from combustion products from the oxygen-fired heater ("OFH"). In some embodiments, at least a portion of the second carbon dioxide stream is added as feed to the HS. Use of an OFH also reduces the carbon footprint of the process disclosed herein by capturing carbon dioxide for use as a feed to the HS system, such as to an RWGS reactor, instead of releasing carbon dioxide to the atmosphere such as in the flue gas of conventionally fired heaters.

In some embodiments, in contrast to conventional operation of an OFH, where flue gas comprising $CO_2$ is emitted to the atmosphere, all flue gas from the OFH combustion zone is captured for used in the eFuels plant. $CO_2$ capture and recovery are enhanced by replacing combustion air (predominantly $N_2$) with oxygen. This significantly increases the concentration of $CO_2$ in the flue gas relative to a conventionally fired heater, making capture and recovery much more energy efficient. Furthermore, capturing all flue gas any emissions, including but not limited to $CO_2$, PM, $NO_X$, VOC, and CO.

Oxygen-fired heater reactions and apparatuses useful in the process disclosed herein are described in more detail in U.S. Pub. Nos. 2022/0033324A1, 2018/0237323A1, 2013/0095437A1, 2004/0259045A1; U.S. Pat. Nos. 6,416,317, 5,921,771, 5,516,279, 4,986,748, and 4,954,076; and Oxyfuel combustion for CO2 capture in power plants, https://www.sciencedirect.com/science/article/abs/pii/S1750583615002637; Oxy-Combustion, https://netl.doe.gov/node/7477; Oxy Combustion with CO2 Capture, https://www.globalccsinstitute.com/archive/hub/publications/29761/co2-capture-technologies-oxy-combustion.pdf; and Oxy Combustion Processes for CO2 Capture from Power Plant, https://ieaghg.org/docs/General_Docs/Reports/Report%202005-9%20oxycombustion.pdf, all of which are fully incorporated by reference herein for all jurisdictions in which such incorporation is permitted.

Process Wastewater Treatment

In some embodiments, in addition to environmentally compliant aspects of the core process of producing synthetic hydrocarbons, the process herein includes improvements to peripheral and/or infrastructure processes, such as, but not limited to processing of wastewater.

Historically, process wastewater produced in a FT reactor and/or hydrocracking reactor is treated in a Water Fractionation Unit (WFU) followed by a Bio-Treatment Unit (BTU). The treated water is then typically discharged to local waterways. The BTU also produces a significant bio-sludge stream which requires dewatering and offsite disposal.

The process disclosed herein replaces the BTU with an anaerobic biodigester. This change reduces bio-sludge production, reduces equipment, reduces plot space, and provides a biogas stream ($CO_2$ and $CH_4$), which is recovered and consumed in the HS.

The biogas recovery stream (from the anaerobic biodigester) is added to the HS improving carbon and hydrogen efficiency. Water from the anaerobic biodigester is recovered to the process via the desalinization unit. This improves water efficiency and reduces environmental impact.

In some embodiments, the process implemented in the eFuels plant further comprises feeding wastewater withdrawn from the HS system to an anaerobic biodigester. Anaerobic biodigestion conditions are implemented in the anaerobic biodigester to convert the process wastewater stream to a first gas product stream, a first treated water stream, and a first digestate solid. The first gas product stream comprises carbon dioxide, methane, or a combination thereof.

In some embodiments, the process disclosed herein further comprises adding the first treated water stream from the anaerobic biodigester to an aerobic biodigester, wherein the first treated water stream comprises a second organic material. Aerobic biodigestion conditions are implemented in the aerobic biodigester to convert the first treated water stream to a second gas product stream, a second treated water stream, and a second digestate solid. The second treated water stream is introduced to the thermal desalination unit as additional feed. Alternately, if the thermal desalination unit is not available, the second treated water stream can be discharge to the seawater outfall.

Integration Efficiency Steps

The foregoing discloses and describes processing units, an arrangement of processing flow units, and process streams flowing between such processing units in the RFCER system. Various aspects of the processing units, the arrangement of processing flow units, and the process streams flowing between such processing units disclosed herein contribute to a reduced carbon footprint, improved carbon efficiency, improved hydrogen efficiency, and/or improved energy efficiency of the eFuels plant and disclosed herein relative to conventional production of synthetic hydrocarbon fuels.

The disclosed RFCER system provides an ability to continue stable operations of the eFuels plant in spite of fluctuations in the electrical grid, or the stability of the electrical grid, all through providing a plurality of operational modes and an ability to switch between such operational modes while maintaining a stable production rate of synthetic liquid hydrocarbon products from the process of the disclosed invention. Electrical flexibility is provided by deployment of electrolyzer technology and optimal use of hydrogen storage, carbon dioxide storage, SLG storage, and batteries. Emissions are minimized and carbon efficiency is maximized by deployment of oxygen-fired heater technology. Carbon and hydrogen efficiency are maximized by recycling SLG produced by the HS system and gas, comprising methane and/or carbon dioxide, produced by anaerobic wastewater treatment.

In some embodiments, in addition to the carbon efficiency, hydrogen efficiency, and/or energy efficiency of the basic arrangement and operation of the RFCER system, additional incremental improvements in carbon efficiency, hydrogen efficiency, and/or energy efficiency are achieved by Electrical Load Balancing/Electrical Grid Stabilization, Integration of eFuels Plant with External Facilities, Desalination Optimization, Heat Recovery from Electrolysis Unit, Oxygen-fired Heater Optimization, Heat Transport to the HS System, Wastewater Containment Flexibility, DAC Optimization, Electrically Heated Steam Boiler.

Electrical Load Balancing/Electrical Grid Stabilization

In some embodiments, the combination of PEMs, AECs, batteries and/or fuel cells, $H_2$ storage, and SLG storage provides a fast response time for electrical load balancing and electrical grid stabilization and a significant range for maximum electrical load to minimum electrical load (i.e., from maximum electrolysis unit rates to shutting down all or a portion of the electrolysis unit or any rate in between for some period).

In some embodiments, batteries and/or fuels cells can activate to maintain electrolysis unit stability even with a nearly instantaneous reduction in power for the electrical supplier (the grid). When grid power is prevalent, electricity can by routed to charge batteries to be ready for low power excursion of the grid or when grid power is more limited.

In some embodiments, SLG withdrawn from storage can be added to the HS system to reduce $H_2$ feed requirements to the HS systems. This provides another measure to permit turning down electrolysis unit rates with minimal or no effect on HS system operations. Alternatively, SLG withdrawn from storage can be added to the HS system while maintaining electrolysis unit rates and HS system rates constant, thus allowing production of excess $H_2$ to build inventory in $H_2$ storage. Alternatively, $H_2$ rates to the HS system, from electrolysis unit production, $H_2$ storage, or combination thereof, can be maximized to back out SLG feed to the HS system and permit building SLG inventory.

In some embodiments, $CO_2$ production rates and addition to or withdrawal from $CO_2$ storage can be varied independently from $H_2$ production rates and addition to or withdrawal from $H_2$ storage while maintaining the required ratio of $CO_2$ and $H_2$ feed to the HS system. This allows strategic control of both $CO_2$ and $H_2$ inventories to further isolate HS system operations from grid fluctuations.

In some embodiments, any one of the above steps can be taken independently to the minimum or maximum extent for that step individually, or maintained at some intermediate level between the minimum and maximum for a period of time as needed to accommodate grid fluctuations. In some embodiments, any two or more of the above steps can be taken in combination, wherein each step is implemented to its minimum extent, its maximum extent, or any level in between the minimum and maximum, to accommodate larger and/or more extended grid fluctuations.

These control steps, taken individually or in combination, serve to isolate the HS system from short term grid fluctuations and/or provide time for the HS system operations to be controllably adjusted to more extended reductions in grid power.

Integration of eFuels Plant With External Facilities

In some embodiments, the eFuels plant is integrated with an adjacent biomass anaerobic biodigestion plant, where low-grade heat is supplied to facilitate production of renewable methane. Biomass can be any plant-based material including straw, wood chips, bamboo, and agricultural waste. The biodigestion produces a biogas stream which comprises of $CO_2$ and $CH_4$. Purification is used to produce pipeline specification natural gas by removing the $CO_2$. Hence biogenic $CO_2$ is made as a byproduct. To prevent venting, this $CO_2$ is supplied to the eFuels plant as feedstock. Low-grade heat from the eFuels Plant would normally be removed via air cooling. Co-location and heat/$CO_2$ integration improves material, energy, and cost efficiencies for both facilities.

In some embodiments, the steam turbine generator receives excess steam and generates electricity, and the turbine operating conditions are optimized for electricity production. Dependent on the temperature required for low-grade heat export, the STG exhaust pressure can be optimized for production of heat for export to customers.

Desalination Optimization

In some embodiments, the water produced through desalination is used in the process only.

In some embodiments water production is maximized through extended heat integration to enable export to customers.

In some embodiments, the desalination brine is recovered, and in combination with a zero liquid discharge unit, will maximize utilization of heat produced by the process, and remove the environmental impact of the effluent streams when discharged to the environment.

Heat Recovery From Electrolysis Unit

In some embodiments waste heat generated by the electrolysis unit is recovered and either used directly or upgraded using a heat pump system.

In some embodiments, a tempered water loop is used to supply heat for export and thermal desalination. Low-grade heat is first recovered from the electrolysis unit and then increased in temperature using the heat pump heat recovery system. Tempered water returned from users is cooled in the heat pump evaporator and supplied to the electrolysis unit for heat recovery. The heat pump comprises an evaporator, a compressor, a condenser, an expansion valve, and a recirculating heat transfer medium, such as, but not limited to, a high-pressure gas with a low boiling point, such as LPG, ammonia or freon.

The heat pump process begins with the evaporator, which is typically a heat exchanger located to recover waste heat from one or more locations in the electrolysis unit requiring heat removal to control the process. A refrigerant is circulated through the evaporator, absorbing the heat from the process stream and turning it into a low-pressure vapor. The vapor then passes through the compressor, which raises the pressure and temperature of the refrigerant. The high-pressure vapor is then directed to the condenser, which is another heat exchanger located in the thermal desalination unit for use in the desalination process. The refrigerant gives off its heat to the thermal desalination unit, which is at a lower temperature than the waste heat stream. As the refrigerant cools, it condenses back into a high-pressure liquid. The high-pressure liquid then passes through the expansion valve, where the pressure is lowered and the refrigerant is allowed to expand back into a low-pressure vapor, thus completing the heat pump cycle.

This recovered and/or upgraded heat is exported to adjacent users and/or supplied to the thermal desalination unit as a heating medium, thus further improving energy efficiency of the eFuels plant.

Oxygen-Fired Heater Optimization

In some embodiments, a portion of the flue gas produced in the combustion zone of the oxygen-fired heater is cooled and recirculated to the oxygen-fired burner to control the combustion temperature and prevent excessive combustion zone temperatures resulting in mechanical damage (overheating) to flue gas duct heat exchangers.

In some embodiments, the flue gas generated in the combustion zone of the oxygen-fired heater is cooled to condense water from the flue gas exiting the oxygen-fired heater. The condensed water is separated from the cooled flue gas and is recovered as additional feed to the desalination process. Recovery of OFH condensed water reduces the plant seawater consumption.

In some embodiments, when the HS is offline at least a portion or all of the anaerobic biodigester biogas stream, comprising methane and carbon dioxide, is sent as a fuel to the combustion zone of the oxygen-fired heater. The biogas combustion provides heat and $CO_2$ for recovery. Since oxygen is used in the combustion of fuel instead of air, no additional $N_2$ is added to the combustion zone to generate additional $NO_x$.

Heat Transport to the HS System

In some embodiments, a portion of the superheated steam is provided to the HS system to provide heat to one or more processes in the HS system. This reduces or removes the requirement for one or more conventional fired heaters in the HS system. In combination with the OFH, this eliminates fired point sources thus reducing flue gas emissions comprising carbon dioxide and other criteria pollutants to the environment including nitrogen oxide compounds ($NO_x$).

Wastewater Containment Flexibility

In some embodiments, if the anaerobic biodigester is offline, the process wastewater stream, comprising a first organic material, can be bypassed and fed directly to the aerobic biodigester, maintaining treatment capacity and keeping discharged water within discharge limits.

In some embodiments, intermediate tank storage is included downstream of the HS systems and upstream of the anaerobic biodigestion unit to act as a buffer between the HS system and the anaerobic biodigestion unit. This buffer ensures a consistent quality of feed to the anaerobic biodigestion unit, thus improving reliability of the anaerobic biodigestion unit and consistency of the treated water product from the anaerobic biodigestion unit. The intermediate tank storage also allows streams containing organic material to be diverted to the OFH if the anaerobic biodigestion unit is unavailable. This further enhances operational flexibility and efficiency of both the wastewater system and the eFuels plant. The storage tanks also allow the anaerobic digestor to be bypassed and wastewater streams from the HS system to instead be fed directly to the aerobic system, further improving operational flexibility and efficiency of both the wastewater system and the eFuels plant.

DAC Optimization

In some embodiments, the DAC unit can be co-located and integrated with the HS system and RFECR for exchange of heat and maximum energy efficiency. The DAC unit removes $CO_2$ from air into a liquid or solid substrate. To desorb $CO_2$, the DAC substrate or liquid is heated producing a $CO_2$ stream. This stream is then cooled, compressed, and purified. The DAC unit requires low-grade heat for the desorption of $CO_2$ and other utilities. The HS produces surplus low-grade heat in the form of hot water which can be provided for DAC desorption. The OFH $CO_2$ compression and purification can also be integrated with the DAC unit for treatment of the DAC produced $CO_2$. This integration improves the overall energy and cost efficiency of the DAC and eFuels Plant.

Electrically Heated Steam Boiler

In some embodiments, an electrically heated steam boiler (eBoiler) is used to supply pressurized steam for start-up, shutdown, and normal operation. Boiler feed water is supplied to the eBoiler from the boiler feed water pump. Steam is produced between the electrodes within the eBoiler steam drum. Steam accumulates in the upper part of the steam drum and is released to the eFuels Plant steam system through the main steam valve. The eBoiler replaces the traditional natural gas fired boiler removing an emissions source, further reducing the carbon and pollutant footprint of the eFuels plant.

Alternate Configurations of the eFuels Plant

In alternate embodiments of the process disclosed herein, eMethanol and related products are produced instead of SLG, SLD, SMD, and SHD. In these embodiments, a methanol synthesis (MS) system is substituted for the HS system, such that an eMethanol plant comprises a RFCER system and a MS system. The MS system comprises a syngas unit, methanol synthesis unit, and methanol purification (distillation). Products withdrawn from the MS system include: 1) topping column light products including TMA, etc. (analogous to SLG from HS system); 2) methanol from refining column (analogous to SLD from HS system); 3) fusel oil from refining column including ethanol, butanol, and/or DME (analogous to SMD from HS system); and refining column bottoms comprising water (analogous to SHD from HS system). In some embodiments, purge gas from methanol synthesis is sent to OFH as fuel. High pressure steam from the MS syngas unit, and medium pressure steam from the MS methanol synthesis are sent to the OFH for superheating. Steam/heat is provided to the MS methanol purification for methanol refining. Process wastewater from the MS system is sent to the anaerobic unit.

In alternate embodiments of the process disclosed herein, eGasoline and related products, such as eKerosene, are produced instead of SLG, SLD, SMD, and SHD. In these embodiments, a gasoline synthesis (GS) system is substituted for the HS system, such that an eGasoline plant comprises a RFCER system and a GS system. The GS system comprises the units described above in a MS system plus a methanol-to-gasoline (MTG) reactor and/or a methanol-to-kerosene (MTK) reactor to produce gasoline and/or kerosene from methanol/DME. To produce eChemicals, comprising fine chemicals (e.g., cosmetics and pharmaceuticals) and other chemical products (solvent feedstock, detergent feedstock, base oil waxes, Fischer-Tropsch liquids as synthetic crude oil) the GS refining section can be modified by introducing one or more of the following: vacuum distillation columns, isomerization reactor, hydrogenation reactor, and/or normal paraffin extraction units to produce solvent feedstock, detergent feedstock, base oil waxes, and/or Fischer-Tropsch liquids as synthetic crude oil.

Carbon Efficiency

In some embodiments, the process implemented in an eFuels plant as described herein produces one or more synthetic hydrocarbon products which have a carbon dioxide intensity of less than a few percent to approximately zero.

Certain Embodiments

In some embodiments, a process for producing one or more synthetic hydrocarbon products, comprises:

a) adding a first amount of electrical load and a first corresponding water feed stream rate to an electrolysis unit under reaction conditions sufficient to form a first hydrogen stream and an oxygen stream, wherein the electrolysis unit:
   i) comprises one or more alkaline electrolysis cells (AECs), one or more proton exchange membrane cells (PEMs), or a combination thereof; and
   ii) is capable of changing to a second amount of electrical load and a second corresponding water feed stream rate at a rate of change greater than or equal to 0.1%/sec, wherein 100% is the maximum electrical load of the electrolysis unit;
b) feeding at least a portion of the first hydrogen stream and a carbon dioxide stream to a hydrocarbon synthesis (HS) system;
c) implementing synthesis conditions in the HS system sufficient to produce hydrocarbon products; and
d) recovering hydrocarbon products comprising a synthetic liquefied gas (SLG).

In some embodiments, in addition to the foregoing limitations of the process, the process is further characterized by one or more of the following:

a) the hydrocarbon products further comprise a synthetic light distillate (SLD), a synthetic middle distillate (SMD), a synthetic heavy distillate (SHD), or a combination thereof;
b) the first and second amounts of electricity are provided by an electrical grid powered by one or more renewable energy sources, wherein in further embodiments, the one or more renewable energy sources comprise solar energy, wind energy, hydroelectric energy, geothermal energy, biomass combustion, nuclear energy, tidal energy, wave energy, hydrogen fuel cells, seawater fuel cells, or a combination thereof;

c) the carbon dioxide stream comprises:

i) carbon dioxide imported from a source external to the process, wherein in further embodiments, the source external to the process comprises:

(1) anaerobic digestion of biomass;

(2) combustion of biomass or biogas to recover carbon dioxide; or (3) a combination thereof;

ii) producing carbon dioxide with a direct air capture unit;

iii) producing carbon dioxide with an anaerobic biodigester;

iv) producing carbon dioxide as a combustion product of an oxygen-fired heater;

v) withdrawing carbon dioxide from a carbon dioxide storage system; or vi) a combination thereof;

d) the process further comprises:

i) introducing at least a portion of the first hydrogen stream to a hydrogen storage facility, wherein in further embodiments, a second hydrogen stream is withdrawn from the hydrogen storage facility as feed to the hydrocarbon synthesis system;

ii) introducing at least a portion of the carbon dioxide stream to a carbon dioxide storage facility;

iii) introducing at least a portion of the synthetic liquefied gas (SLG) to a SLG storage facility, wherein in further embodiments, a SLG stream is withdrawn from the SLG storage facility, recycled from the hydrocarbon synthesis system, or a combination thereof, as feed to the hydrocarbon synthesis system; or iv) a combination thereof;

e) the process further comprises:

i) adding sea water to a thermal desalination unit under desalination conditions to produce a desalinated water effluent, wherein in further embodiments, the thermal desalination unit additionally produces a brine stream, and in yet further embodiments the brine stream is treated in a salt recovery unit to produce potable water stream and a salt product;

ii) adding the desalinated water effluent to a demineralization unit under demineralization conditions to produce a demineralized water effluent; and iii) withdrawing a first portion of the demineralized water effluent as the water feed stream to the electrolysis unit, wherein in further embodiments:

(1) a second portion of the demineralized water effluent is introduced to a deaeration unit to produce a boiler feed water stream; and (2) the boiler feed water stream is sent to the hydrocarbon synthesis system as a cooling medium for one or more process units in the hydrocarbon synthesis system, wherein in further embodiments, the cooling medium is converted to one or more steam streams in the HS system;

f) the process further comprises:

i) adding combustion reactants to an oxygen-fired heater (OFH), wherein:

(1) the oxygen-fired heater comprises a combustion zone and a heating zone; and (2) the combustion reactants comprise at least: a portion of the oxygen stream from the electrolysis unit; and HS system purge gas, HS system off gas, SLG, or a combination thereof;

ii) combusting the combustion reactants in the combustion zone of the OFH to produce heat and a combustion product, comprising carbon dioxide;

wherein in further embodiments, the process further comprises one or more of:

adding at least a portion of the combustion product to the combustion zone to control the temperature of the combustion zone;

recovering water from the combustion product; and introducing at least one of the one or more steam streams from the HS system to the heating zone of the oxygen-fired heater to produce one or more superheated steam streams, wherein in further embodiments: at least a portion of the one or more superheated steam streams is introduced to a steam turbine generator to produce generated electricity and a steam condensate stream; at least at portion of the one or more superheated steam streams is sent to the HS system to provide heat to one or more process units in the HS system; or a combination thereof; wherein in further embodiments: at least a portion of the generated electricity utilized in the eFuels plant, and the steam condensate stream is introduced to the demineralization unit as additional feed; and g) the process further comprises:

i) adding a process wastewater stream to an anaerobic biodigester, wherein the process wastewater stream comprises a first organic material;

ii) implementing anaerobic biodigestion conditions in the anaerobic biodigester;

iii) withdrawing a first gas product stream and a first treated water stream, wherein the first gas product stream comprises carbon dioxide, methane, or a combination thereof; and iv) adding the first gas product stream to: the hydrocarbon synthesis system as feed to one or more units in the HS system; the oxygen-fired heater as a combustion reactant; or a combination thereof; wherein in further embodiments, the process further comprises:

(1) adding the first treated water stream from the anaerobic biodigester to an aerobic biodigester, wherein the first treated water stream comprises a second organic material;

(2) implementing aerobic biodigestion conditions in the aerobic biodigester;

(3) withdrawing a second treated water stream and a digestate solid; and (4) adding the second treated water stream as additional feed to the thermal desalination unit.

In some embodiments, in addition to the foregoing limitations of the process, the process further comprises:

a) recovering an amount of excess heat from the electrolysis unit, the stream turbine generator, or a combination thereof; and b) delivering at least a portion of the amount of excess heat to the thermal desalination unit, the direct air capture unit, an export disposition, or a combination thereof;

wherein in further embodiments, recovering and/or delivering are implemented in a heat integration system comprising one or more heat pumps.

In some embodiments, an eFuels production system, comprises:

a) an electrolysis unit to react electricity and a water feed stream in the presence of an electrolysis catalyst to form hydrogen and oxygen, wherein the electrolysis unit:
   i) comprises one or more alkaline electrolysis cells (AECs), one or more proton exchange membrane cells (PEMs), or a combination thereof; and
   ii) is capable of changing from a first amount of electrical load to a second amount of electrical load and from a first amount of water feed rate, corresponding to the first amount of electrical load, to a second amount of water feed rate, corresponding to the second amount of electrical load, at a rate of change greater than or equal to 0.1%/sec, wherein 100% is the maximum electrical load of the electrolysis unit; and
b) a hydrocarbon synthesis (HS) system to convert carbon dioxide and hydrogen to produce one or more of synthetic liquefied gas (SLG), a synthetic light distillate (SLD), a synthetic middle distillate (SMD), and a synthetic heavy distillate (SHD).

In some embodiments, in addition to the foregoing limitations of the system, the system further comprises:

a) a hydrogen storage system, and optionally a hydrogen compression system, to supply hydrogen to the HS system;
b) a carbon dioxide compression and storage system to supply carbon dioxide to the HS system;
c) a synthetic liquefied gas (SLG) compression and storage system to supply SLG to the HS system; or
d) a combination thereof.

In some embodiments, in addition to the foregoing limitations of the system, the system further comprises a direct air capture (DAC) unit to recover carbon dioxide to feed to the HS system.

In some embodiments, in addition to the foregoing limitations of the system, the system further comprises a thermal desalination unit and a demineralization unit to treat sea water to produce the water feed stream.

In some embodiments, in addition to the foregoing limitations of the system, the system further comprises a deaeration unit to receive a portion of the water feed stream and produce a boiler feed water stream.

In some embodiments, in addition to the foregoing paragraphs describing embodiments of the system, the system further comprises an oxygen-fired heater (OFH) adapted for:

a) receiving combustion reactants in a combustion zone to produce heat and an OFH flue gas, comprising carbon dioxide, wherein the combustion reactants comprise a portion of the oxygen from the electrolysis unit and a gas stream, comprising HS system purge gas, HS system off gas, SLG, or a combination thereof, from the HS system; and
b) receiving at least one steam stream from the HS system in a heating zone to produce a superheated steam stream.

In some embodiments, in addition to the foregoing limitations of the system, the system further comprises a steam turbine generator to receive the superheated steam stream from the oxygen-fired heater to produce electricity and a steam condensate stream to be sent as additional feed to the demineralization unit.

In some embodiments, in addition to the foregoing paragraphs describing embodiments of the system, the system further comprises an anaerobic digester to receive a process wastewater stream from the HS system to produce a gas stream and a first treated water stream, wherein the gas stream is recycled to the HS system. In some embodiments, the system further comprises an aerobic digester for receiving the first treated water stream and producing a second treated water stream to be sent as additional feed to the thermal desalination unit.

In some embodiments, a process for producing a hydrogen product stream comprises:

a) operating an electrolysis unit at a first production rate to produce a first hydrogen product stream at a first flow rate, wherein the electrolysis unit is powered by a first electrical load from an electrical power grid corresponding to the first flow rate;
b) reducing the first electrical load from an electrical power grid to a second electrical load from the electrical power grid, wherein the second load is in range of from 0 to 99% of the first electrical power load;
c) in response to the reduction in electrical power load from the electrical power grid:
   i) introducing a third electrical power load from an electrical storage system, comprising one or more batteries, one or more fuel cells, or a combination thereof, wherein the third electrical power load is in the range of from 1% of the first electrical power load to the difference between the first electrical power load and the second electrical power load; and/or
   ii) reducing the first hydrogen product stream to a second flow rate in the range of from 1% of the first flow rate to a flow rate corresponding to the second electrical power load and withdrawing hydrogen from a hydrogen storage system as a second hydrogen product stream at a rate equivalent to the difference between the first flow rate and the second flow rate, wherein a rate of change from the first electrical power load to the second electrical power load is greater than or equal to 0.1%/sec, wherein 100% is a maximum electrical load of the electrolysis unit;

wherein steps i) and/or ii) are implemented to an extent such that the third electrical power load and the withdrawal rate from the hydrogen storage system maintain the hydrogen product stream at a rate equivalent to the first flow rate.

In some embodiments, a process for producing a syngas product stream comprises:

a) feeding the hydrogen feed stream of claim 28 and a carbon dioxide feed stream to a reverse water-gas shift (RWGS) unit to produce a first syngas product stream;
b) converting a synthetic liquified gas (SLG) stream to syngas by partial oxidation and/or steam reforming to produce an additional feed stream to the RWGS unit, wherein the additional feed stream comprises hydrogen and carbon dioxide;
c) introducing the additional feed stream into the RWGS unit;
d) reducing the hydrogen feed stream by a first amount and reducing the carbon dioxide feed stream by a second amount to maintain production of the first syngas product stream; and
e) adding the first amount of hydrogen to the hydrogen storage system.

In some embodiments, the syngas product stream of the foregoing paragraph is fed to:

a) a Fischer-Tropsch unit followed by hydrocracking or isomerization to produce synthetic light distillate, synthetic middle distillate, and/or synthetic heavy distillate;

b) a methanol synthesis unit to produce methanol; or c) a methanol synthesis unit followed by a methanol-to-gasoline reactor to produce gasoline; or d) a methanol-to-kerosene reactor to produce kerosene.

Although the disclosed process and system have been described in detail, it should be understood that various changes, substitutions and alterations can be made herein without departing from the spirit and scope of the invention as defined by the appended claims. Moreover, the scope of the present application is not intended to be limited to the particular embodiments of the processes, machines, compositions, means, methods, and/or steps described in the specification. As one of the ordinary skill in the art will readily appreciate from the present disclosure, processes, machines, compositions, means, methods, and/or steps, presently existing or later to be developed that perform substantially the same function or achieve substantially the same result as the corresponding embodiments described herein, may be utilized according to the present invention. Accordingly, the appended claims are intended to include within their scope such processes, machines, compositions, means, methods, and/or steps.

EXAMPLES

The following investigations and examples are intended to be illustrative only, and are not intended to be, nor should they be construed as limiting the scope of the present invention in any way. Overall energy efficiency is improved by maximizing deployment of heat integration between subprocesses of the overall process. Such process integration solutions have been achieved by comprehensive integrated process modelling. The model combines the standard inputs received from the various core technologies deployed with a complete integrated process model of all auxiliary processes.

Experimental Method

In Examples 1-7, an AspenTech Hysys computer simulation (ASPENTECH HYSYS V12.1 steady-state simulation) of process streams and conditions was used to simulate embodiments of the invention. The simulated process flow diagram ("PFD") is shown in FIG. 1. For brevity and understandability, Table 1, below, reports only selected flow rates and eFuels plant 100 process parameters in order to draw comparisons between different embodiments of the invention (Examples 1-6) and as well as comparison to an HS system operated without an integrated RFCER system as disclosed herein (Example 7). Flow rates and other process parameters of the eFuels plant reported in Table 1 are normalized to the flow rate of imported $CO_2$ 1072 in Example 1 in tonnes per hour—i.e., all flows and process parameters are reported as parts (by weight) wherein stream 1072 in Example 1 is 100 parts (by weight).

Process Flow

A simplified flow diagram of an eFuels plant 1000 is shown in FIG. 1. Flexibility of the RFCER system is demonstrated by different modes of operation in the following examples.

In some embodiments, seawater 1402 is collected and sent as feed to desalinization unit 1010 via stream 1402. Desalinated water product from desalinization unit 1010 is sent to demineralization unit 1020 via stream 1012. Brine remaining after removal of the desalinated portion of the seawater is returned to the sea via stream 1404. Demineralization unit 1020 also receives condensate from steam turbine generator 1290 via stream 1292. A portion of the demineralized water is withdrawn from demineralization unit 1020 and sent as feed to electrolysis apparatus 1030 via stream 1022 and electricity 1440 is added as an input to the electrolysis apparatus 1030, wherein water is separated into hydrogen ($H_2$) stream 1032 and oxygen ($O_2$) stream 1034. In some embodiments, fresh water stream 1406 can supplement or replace stream 1036 as feed to electrolysis unit 1030.

A portion of the demineralized water is withdrawn from demineralization unit 1020 and sent as feed to the deaerator unit 1270 via stream 1024. Boiler feedwater is withdrawn from deaerator unit 1270 via stream 1272 and routed to the HS system 1200 to serve as a heat removal medium (boiler feedwater) for one or more process units in the HS system 1200. Stream 1272 is shown as a single boiler feedwater stream delivered to the HS system and returned from the HS system as single stream 1124 of steam returning from the HS system 1200 back to the RFCER system. In some embodiments, boiler feedwater stream 1272 and/or steam stream 1124 can each be a network of piping.

Oxygen ($O_2$) is withdrawn from electrolysis apparatus 1030 and sent to the oxygen-fired heater (OFH) 1280 via stream 1034. Hydrogen ($H_2$) stream 1032 is routed to hydrogen storage system (and optionally hydrogen compression system) 1040. The block in FIG. 1 designated hydrogen storage system (and optionally hydrogen compression system) 1040 represents high-pressure hydrogen and compression capacity as required to feed hydrogen to the HS system 1200 directly via stream 1042 and/or store hydrogen in storage facilities within block 1040 at a pressure sufficient to feed to the HS system 1200. High-pressure hydrogen is sent from hydrogen storage system (and optionally hydrogen compression system) 1040 via stream 1042 to the hydrocarbon synthesis system 1200, primarily as feed to a RWGS unit and a hydrocracking unit.

Heat is removed from the electrolysis unit 1030 via stream 1036 to heat integration facilities 1295. Heat is supplied integration facilities 1295 from the steam turbine generator condensate stream 1298. Heat is supplied to desalination unit 1010 via stream 1296, DAC unit 1070 via stream 1297, and/or exported from the eFuels plant via stream 1018. Heat is transported by recirculation of one or more closed loop water streams to remove heat from processes generating heat and delivering heat to processes absorbing heat via water in streams 1036, 1298, 1296, 1297, and 1018. In other embodiments, such closed loops may circulate any convenient heat transfer fluid.

Carbon dioxide is sourced by importing from a source 1090 external to the eFuels plant, such as, but not limited to, generation by degradation of biomass, or onsite production by direct air capture 1070. Carbon dioxide is routed to carbon dioxide compression and storage 1080 via stream 1072. High pressure carbon dioxide is sent from $CO_2$ compression and storage 1080 via stream 1082. The block in FIG. 1 designated $CO_2$ compression and storage 1080 represents high pressure $CO_2$ and compression capacity as required to feed $CO_2$ to the HS system 1200 directly via stream 1082 and/or store $CO_2$ in storage facilities within block 1080 at a pressure sufficient to feed to the HS system 1200. High pressure $CO_2$ is sent from $CO_2$ compression and storage 1080 via stream 1082 to the hydrocarbon synthesis system 1200, primarily as feed to a RWGS unit.

Oxygen stream 1034 is fed to the combustion zone of the OFH 1280 along with a fuel stream 1126, comprising purge gas, off gas, or a combination thereof from the HS system 1200. Optionally, SLG from SLG storage 1210 is sent via stream 1214 as additional fuel to the combustion zone of the OFH 1280. Combustion products comprising $CO_2$ are withdrawn from the combustion zone of the OFH 1280 as stream 1282. Stream 1282 is then sent $CO_2$ compression and storage for further processing consistent with the other $CO_2$ sources.

Steam stream 1124 from the HS system 1200 is fed to the heating zone of the OFH 1280 where heat generated in the combustion zone is added to form superheated steam. Superheated steam is delivered to steam turbine generator 1290 via stream 1284 to produce electricity 1294 for use by one or more process units in the RFCER system and/or the HS system 1200. Superheated steam is delivered to the HS system 1200 via stream 1286 to supply heat to one or more process units in the HS system 1200.

Synthetic hydrocarbon product streams, SLG stream 1202, SLD stream 1204, SMD stream 1206, and SHD stream 1208, are withdrawn from the hydrocarbon synthesis system 1200. SLD stream 1204, SMD stream 1206, and SHD stream 1208 are sent to storage and/or distribution by shipping, trucking, and/or pipeline. SLG stream 1202 is sent to the hydrocarbon synthesis system 1200 via stream 1212 as feed to the RWGS unit and/or as fuel to the oxygen-fired heater 1280 via stream 1214.

Process wastewater stream 1242 is withdrawn from the hydrocarbon synthesis system 1200 via stream 1242 as feed to the anaerobic biodigester unit 1250. Gas stream 1254 is withdrawn from the anaerobic biodigester unit 1250 and sent to the hydrocarbon synthesis system 1200, primarily as feed to the RWGS unit. All or a portion of gas stream 1254 can be routed via stream 1255 as fuel to the OFH 1280. Treated wastewater stream 1252 is withdrawn from the anaerobic biodigester unit 1250 and sent as feed to the aerobic biodigester unit 1260. Stream 1243 is a bypass around anaerobic biodigester unit 1250 and only has flow when the anaerobic biodigester unit 1250 is out of service. Treated wastewater stream 1262 is withdrawn from the aerobic biodigester unit 1260 and sent as feed to the thermal desalination unit 1010 and/or to outfall 1264. In some embodiments, clean water is exported outside the eFuels plant 1000 via stream 1014.

In some embodiments, excess heat 1018 remains after heat exchange occurring in heat integration facilities 1295 and can be exported outside the eFuels plant.

Figure 2:
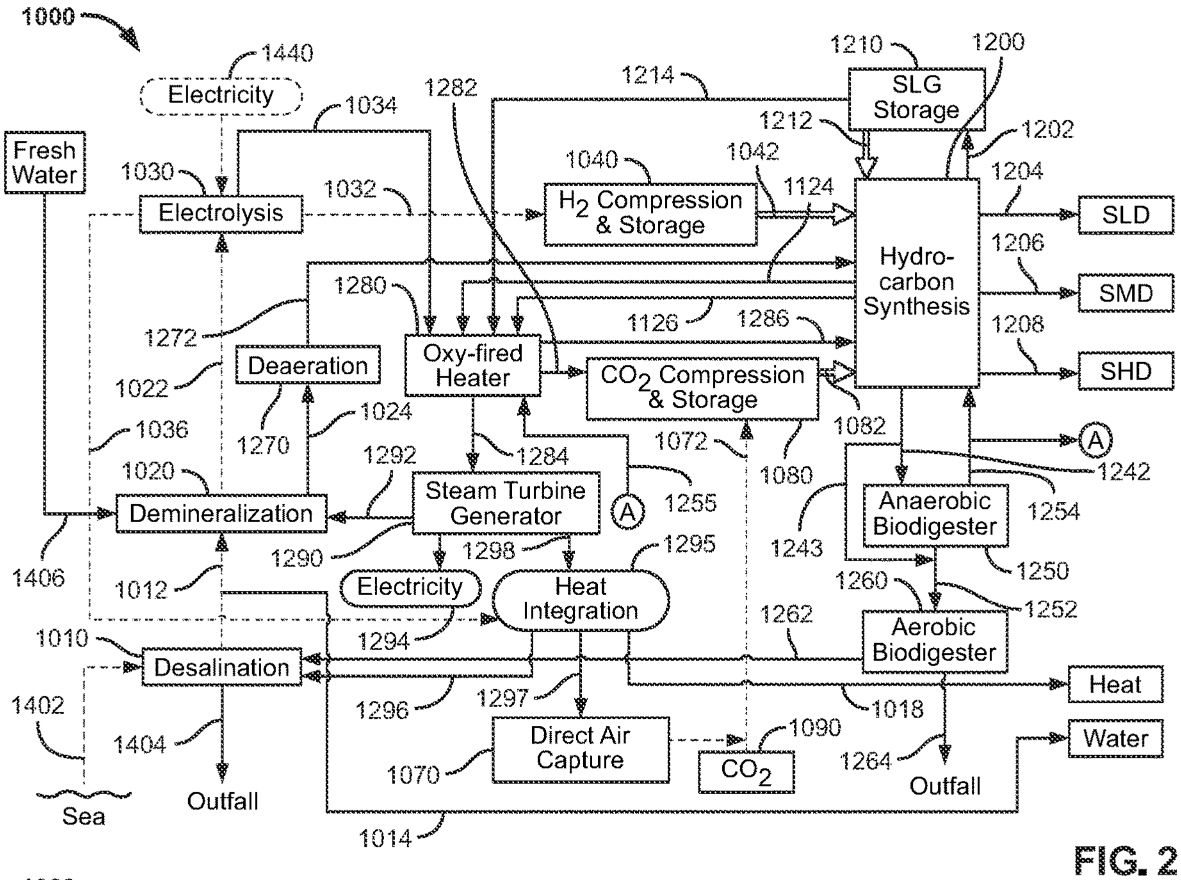
FIG. 2 is a block diagram of an exemplary eFuels plant highlighting significant changes to normal operations for implementing embodiments of the process disclosed herein, wherein hydrogen, carbon dioxide, and synthetic liquefied gas feed streams within the plant are withdrawn from storage facilities.
Figure 3:
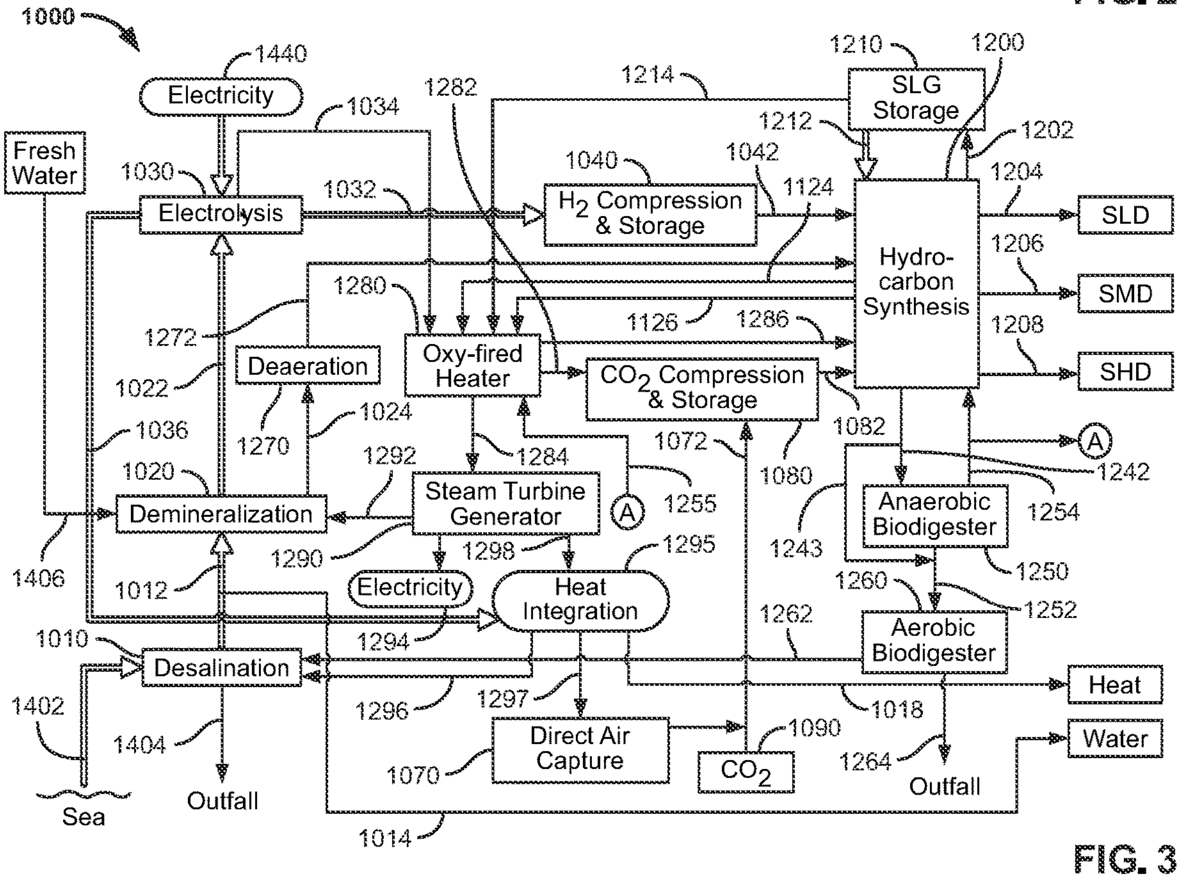
FIG. 3 is a block diagram of an exemplary eFuels plant highlighting significant changes to normal operations for implementing embodiments of the process disclosed herein, wherein hydrogen inventory is built in storage facilities.
Figure 4:
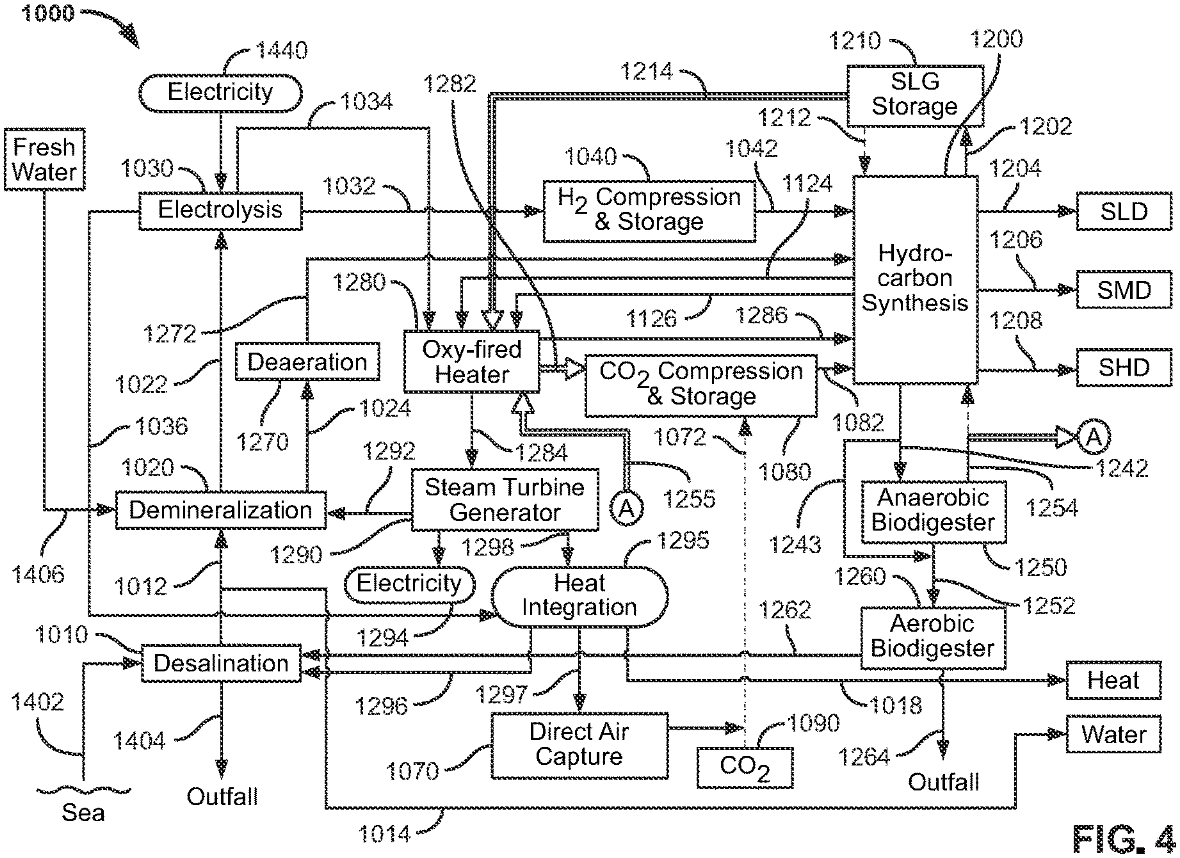
FIG. 4 is a block diagram of an exemplary eFuels plant highlighting significant changes to normal operations for implementing embodiments of the process disclosed herein, wherein anaerobic biodigester biogas and synthetic liquefied gas are routed to maximize fuel to an oxygen-fired heater.
Figure 5:
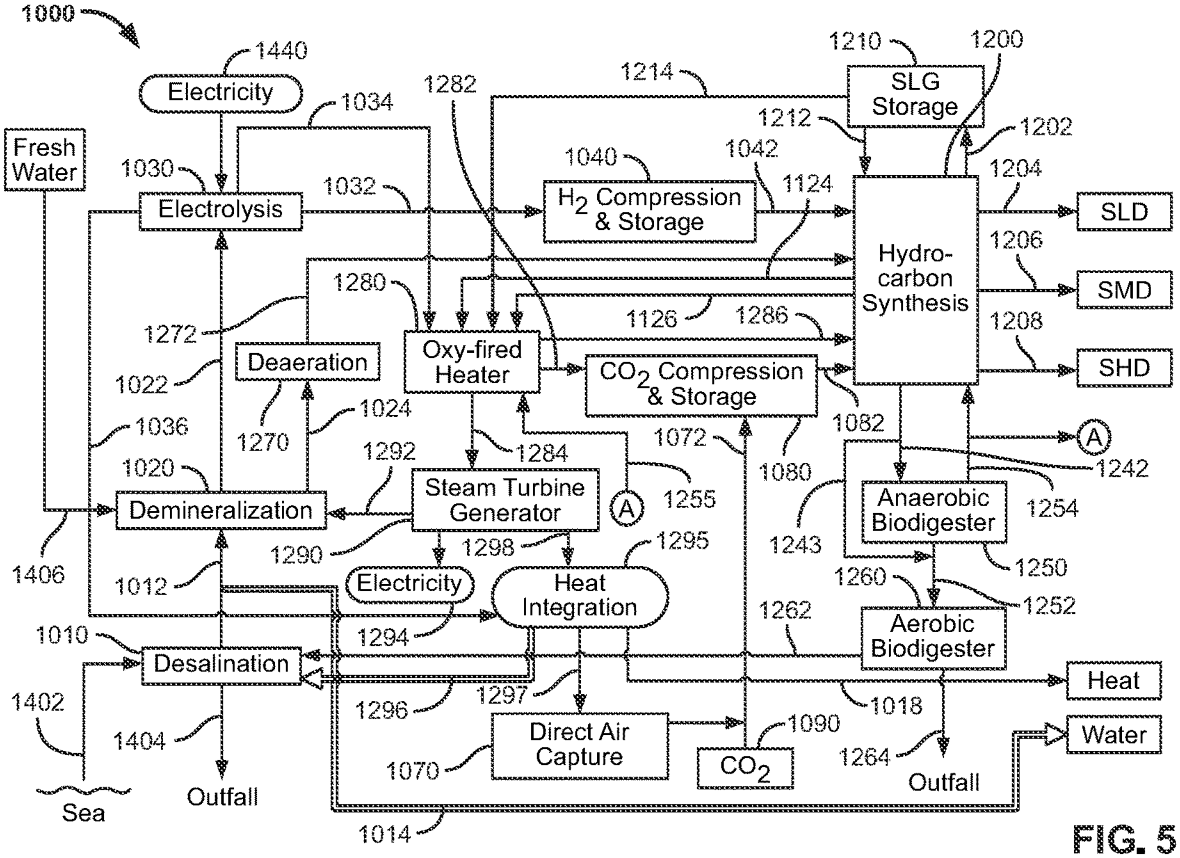
FIG. 5 is a block diagram of an exemplary eFuels plant highlighting significant changes to normal operations for implementing embodiments of the process disclosed herein, wherein thermal desalination is maximized to export desalinized water from the eFuels plant.
Figure 6:
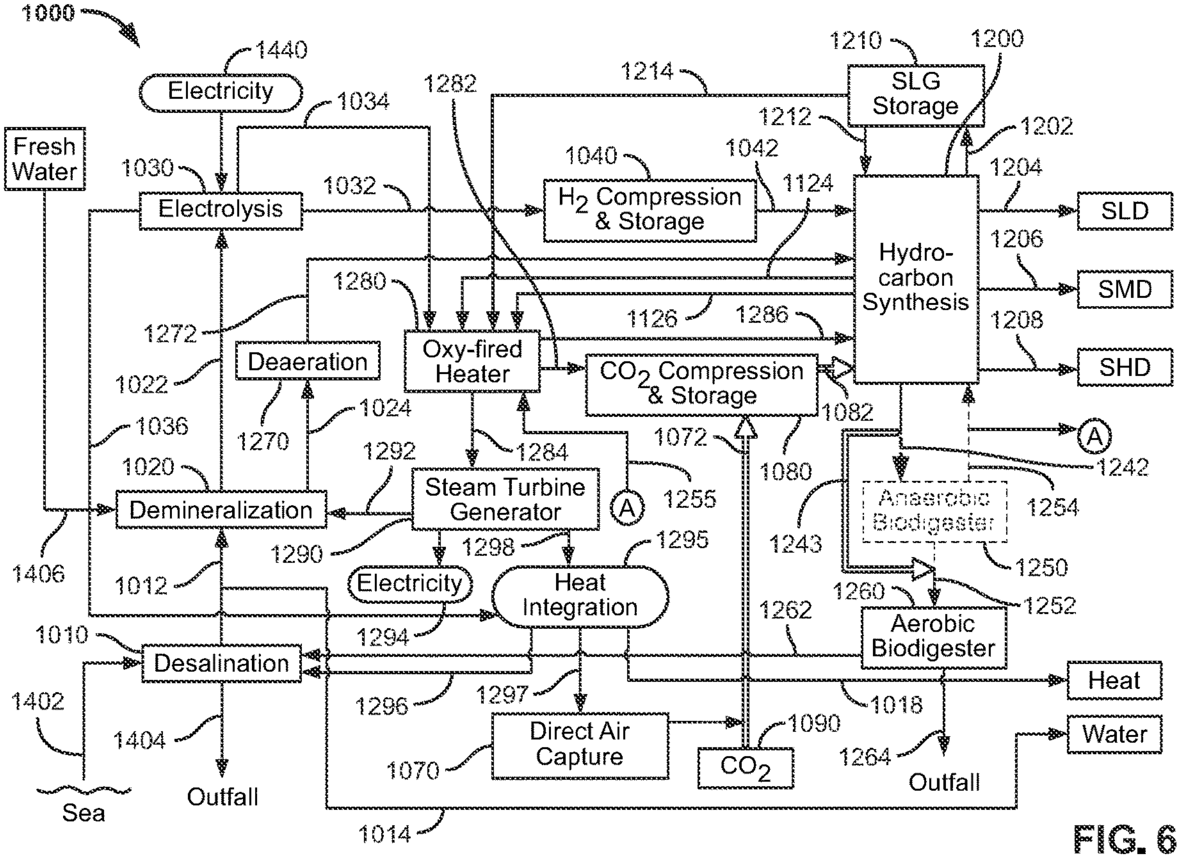
FIG. 6 is a block diagram of an exemplary eFuels plant highlighting significant changes to normal operations for implementing embodiments of the process disclosed herein, wherein an anaerobic biodigester is removed from the process flow.
Figure 7:
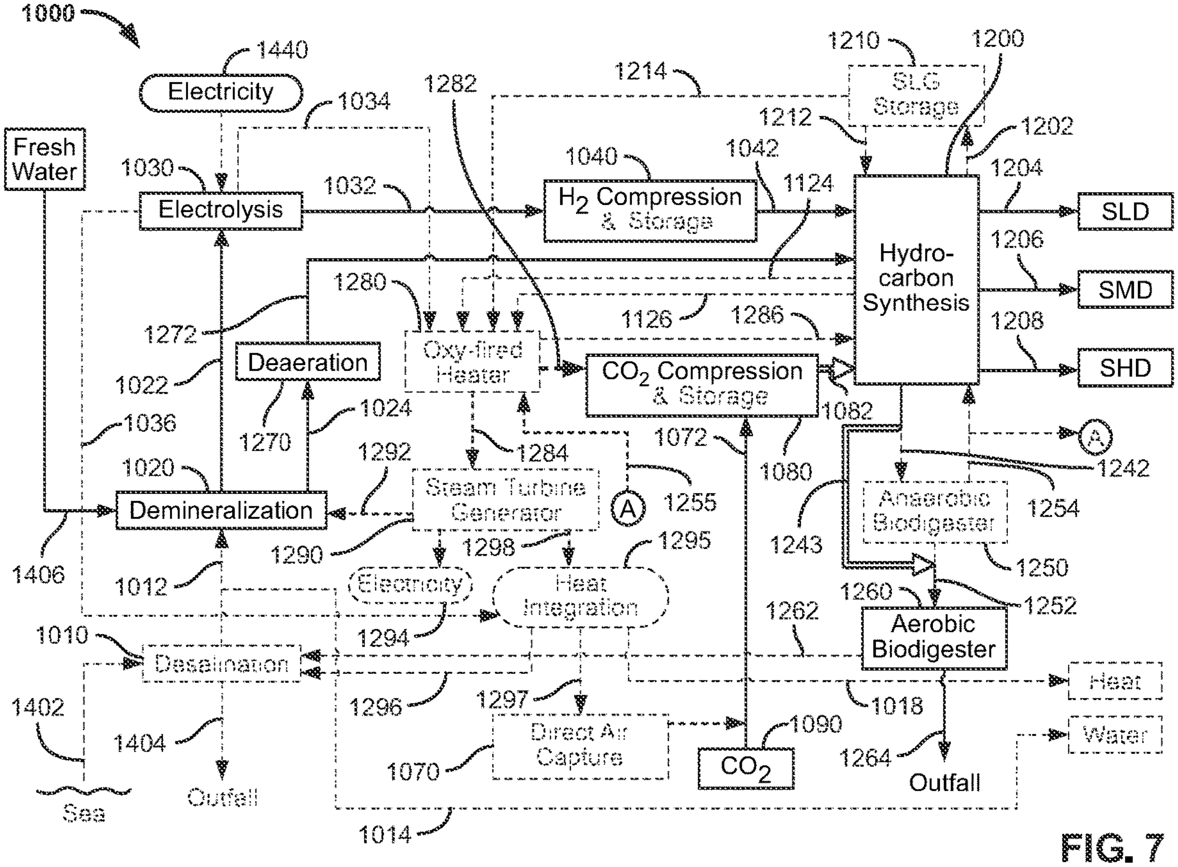
FIG. 7 is a block diagram of a comparative eFuels plant highlighting significant changes to normal operations shown in FIG. 1 in order to simulate a process not having the process improvements disclosed herein.

Table 1 summarizes selected process parameters for various operating regimes of the eFuels plant 1000:

- Example 1, shown in FIG. 1, is a base case operation of the process disclosed herein.
- Example 2, shown in FIG. 2, is a configuration of the disclosed process wherein withdrawal of hydrogen, carbon dioxide, and synthetic liquefied gas from their respective storage systems is maximized.
- Example 3, shown in FIG. 3, is a configuration of the disclosed process wherein $H_2$ to the $H_2$ storage system is maximized.
- Example 4, shown in FIG. 4, is a configuration of the disclosed process wherein biogas from the anaerobic biodigester and SLG from storage to the oxygen-fired heater are maximized.
- Example 5, shown in FIG. 5, is a configuration of the disclosed process wherein production of potable water from the thermal desalination is maximized.
- Example 6, shown in FIG. 6, is a configuration of the disclosed process wherein the anaerobic biodigester is out of service.
- Example 7, shown in FIG. 7, is a comparative example wherein fresh water to fed to an electrolysis unit to produce hydrogen feed to the HS system, wherein other process units of the RFCER system are not present and the associated carbon and energy efficiency steps are not implemented.

Details of these operating regimes are discussed below. Values in Table 1 are normalized where flows are in parts by weight and electrical usage and heat duties are in MW·hr/t.

TABLE 1

| Process | FIG. 1 | | Example | | | | | | |
|---|---|---|---|---|---|---|---|---|---|
| Parameter | reference nos. | Units[1] | 1 | 2 | 3 | 4 | 5 | 6 | 7 |
| $CO_2$ Imported[3] | 1072 | parts | 100.0 | 0.0 | 98.7 | 100.3 | 100.0 | 100.0 | 104.0 |
| $CO_2$ From Storage | 1080[4] | parts | 0.0 | 100.0 | 0.0 | 0.0 | 0.0 | 0.0 | 0.0 |
| $H_2$ from Electrolysis Unit | 1032 | parts | 15.2 | 0.5 | 15.9 | 15.2 | 15.2 | 15.2 | 15.2 |
| $H_2$ from Storage | 1040[4] | parts | 0.0 | 14.7 | 0.0 | 0.0 | 0.0 | 0.0 | 0.0 |
| SLG from Storage | 1212 | parts | 0.0 | 0.4 | 0.4 | 0.0 | 0.0 | 0.0 | 0.0 |
| Seawater Feed | 1402 | parts | 6,203 | 3,535 | 6,175 | 6,318 | 13,297 | 6,200 | 0.0 |
| Seawater Outlet | 1404 | parts | 6,084 | 3,607 | 6,045 | 6,209 | 8,707 | 6,083 | 55.9 |
| Freshwater Feed | 1406 | parts | 0.0 | 0.0 | 0.0 | 0.0 | 0.0 | 0.0 | 158.7 |
| Electrical Power | 1440-1294 + other[5] | MW · hr/t | 1149 | 272.0 | 1204 | 1143 | 1219 | 1148 | 1,100 |
| Cooling Water Duty | not shown | MW · hr/t | 64.8 | 36.4 | 64.2 | 66.4 | 91.6 | 64.8 | 68.6 |
| SLD Production | 1204 | parts | 4.7 | 4.8 | 4.7 | 3.9 | 4.7 | 4.7 | 4.8 |
| SMD Production | 1206 | parts | 26.8 | 26.8 | 26.8 | 26.8 | 26.8 | 26.8 | 25.9 |
| SHD Production | 1208 | parts | 0.0 | 0.0 | 0.0 | 0.0 | 0.0 | 0.0 | 0.0 |
| Desalinated Water Export | 1014 | parts | 0.0 | 71.8 | 0.0 | 0.0 | 2,865 | 0.0 | 0.0 |

TABLE 1-continued

| Process Parameter | FIG. 1 reference nos. | Units[1] | Example 1 | 2 | 3 | 4 | 5 | 6 | 7 |
|---|---|---|---|---|---|---|---|---|---|
| Heat Exported | 1018 | MW·hr/t | 271.4 | 271.4 | 271.4 | 271.4 | 0.0 | 271.4 | 0.0 |
| $CO_2$ Emitted | not shown | parts | 0.0 | 0.0 | 0.0 | 0.0 | 0.0 | 0.0 | 7.705E−02 |
| Criteria Pollutants Emitted[2] | not shown | parts | 0.0 | 0.0 | 0.0 | 0.0 | 0.0 | 0.0 | 1.932E−05 |

[1]Normalized to flow rate of $CO_2$ imported in Example 1 in tonnes per hour and reported as parts by weight
[2]PM2.5, PM10, VOC, $NO_x$, and $SO_x$
[3]"Imported" includes imported from outside the eFuels plant or produced from DAC
[4]"Storage" is within box and not shown specifically in Figures
[5]"Other" is net electricity used in operating the includes imported from outside the eFuels plant or produced from DAC

Example 1

FIG. 1 depicts a base case of normal operations of an eFuels plant comprising a RFCER system integrated with a HS system. Table 1 shows that for 100 parts $CO_2$ consumed in the operation of the eFuels plant, 26.8 parts of SMD (e.g., jet fuel) and 4.7 parts of SLD are produced with no $CO_2$ or criteria pollutants emitted. Criteria pollutants comprise particulate matter (PM2.5 and PM10), volatile organic compounds, nitrogen oxides, and sulfur oxides.

Equipment, streams, and reference numbers are the same in FIG. 2-FIG. 7 as in FIG. 1, since FIG. 2-FIG. 7 represent the same eFuels plant in different modes of operation. Highlighting of streams in FIG. 2-FIG. 7 denotes changes in particular flow streams relative to the base case operation shown in FIG. 1 where certain flow streams are increased or maximized (double lines) and other flow streams are decreased or stopped completely (dashed lines). Some streams in FIG. 1 base case operation may have no flow in such base case operation but are shown in order to make comparisons to altered operations in FIG. 2-FIG. 7. FIG. 1-FIG. 7 show simplified flows for brevity and clarity. Although only certain reference numbers are mentioned in the discussion of FIG. 2-FIG. 7, all reference numbers are retained for clarity and convenience when comparing figures. One of ordinary skill in design of petrochemical facilities would recognize the need for and appropriate arrangement of piping, valves, heat exchangers, distillation columns, and other common equipment required to implement the process disclosed herein.

Example 2

FIG. 2 depicts a scenario where electrolysis unit rates are minimized to supply $O_2$ to OFH 1034 minimizing the need to operate the thermal desalinization unit 1010. Highlighted streams 1042 and 1082 indicate hydrogen and $CO_2$, respectively, supplied to the HS system 1200 from different sources than base case Example 1. Highlighted stream 1212 indicates an increase in flow of SLG from storage supplied to the HS system 1200 relative to base case Example 1.

Electrolysis unit 1030 rates are reduced to the minimum rate required to produce oxygen to maintain operation of the oxygen-fired furnace via stream 1034. Reduced electrolysis unit rates reduce the flow of hydrogen in stream 1032, and hydrogen is withdrawn from storage via stream 1042 to satisfy the shortfall in hydrogen production due to the reduced electrolysis unit rates. $CO_2$ from import and/or DAC production of $CO_2$ is replaced by 100 parts $CO_2$ from storage. A portion of SLG is withdrawn from storage via line 1212 to maintain balanced operation of the RWGS reactor and resulting production of SMD 1206. Electrolysis unit utility rates (heat, electricity, and water) are all increased. Flows in highlighted streams 1402 and 1012 are shut down along with the thermal desalination unit indicating a significant change from base case Example 1. Highlighted electricity 1440 to electrolysis unit 1030 and stream 1036 to heat integration 1295 indicate significant decrease versus base case Example 1.

Table 1 shows that for 100 parts $CO_2$ consumed in the operation of the eFuels plant, eFuels plant production of SMD is maintained at 26.8 parts of SMD (e.g., jet fuel) and 4.8 parts of SLD with minimized seawater feed or $CO_2$ imported or produced and with no $CO_2$ or criteria pollutants emitted.

Example 3

FIG. 3 depicts a scenario where $H_2$ storage is filled through use of electrolysis unit overcapacity 1030 and SLG to the HS 1212 from SLG storage 1210. Seawater feed 1402 to the thermal desalination unit 1010 is increased to maximize electrolysis unit 1030 rates. This operation maximizes hydrogen production 1032 and allows storage of excess hydrogen above HS system feed requirements 1042. SLG withdrawal 1212 from SLG storage 1210 to the HS system 1200, such as for additional feed to the RWGS reactor, is maximized as required to permit maximum storage rate of hydrogen in the hydrogen storage system. Electrolysis unit utility rates (heat, electricity, and water) are all increased.

Highlighted streams 1402 and 1022 indicate an increase in seawater feed rate relative to base case Example 1. Highlighting of line 1212 indicates an increase in SLG withdrawn from storage to maintain balanced operation of the RWGS reactor and resulting production of SMD 1206. Highlighted stream 1036 indicates an increase heat exported from the electrolysis unit relative to base case Example 1.

Table 1 shows that for 98.7 parts $CO_2$ consumed in the operation of the eFuels plant, 26.8 parts of SMD (e.g., jet fuel) and 4.7 parts of SLD are produced with no $CO_2$ or criteria pollutants emitted.

Example 4

FIG. 4 depicts a scenario where biogas stream 1255 from the anaerobic biodigester 1250 and SLG stream 1214 from SLG storage 1210 are maximized to fuel the OFH 1280, and no biogas from the anaerobic biodigester 1250 is sent to the HS system 1200 via stream 1254 and no SLG is sent to the HS system 1200 from SLG storage 1210 via stream 1212. Increased recovery of $CO_2$ from the OFH combustion products via stream 1282 permits a reduction in $CO_2$ imports and/or DAC-produced $CO_2$. To the extent that the combination of stream 1282 and stream 1072 exceed HS system $CO_2$ feed requirements, excess $CO_2$ is sent to $CO_2$ storage.

Highlighted streams 1214, 1255, and 1282 indicate an increase in these rates relative to base case Example 1. Highlighting of line 1254, 1072, and 1212 indicate a decrease in these rates relative to base case Example 1.

Table 1 shows that for 100.3 parts $CO_2$ consumed in the operation of the eFuels plant, 26.8 parts of SMD (e.g., jet fuel) and 3.9 parts SLD are produced with no $CO_2$ or criteria pollutants emitted.

Example 5

FIG. 5 depicts a scenario where water production in maximized from the thermal desalination unit 1010. Seawater feed stream 1402 to the thermal desalination unit 1010 is increased to maximize desalinated water export stream 1014. Additional heat is withdrawn from heat integration facilities 1295 and delivered to desalination unit 1010 to support the increased throughput.

Highlighted streams 1402, 1296, and 1014 indicate an increase in these rates relative to base case Example 1.

Table 1 shows that for 100 parts $CO_2$ consumed in the operation of the eFuels plant, 26.8 parts of SMD (e.g., jet fuel) and 4.7 parts of SLD are produced with no $CO_2$ or criteria pollutants emitted.

Example 6

FIG. 6 depicts a scenario where the anaerobic biodigester 1250 is offline. Process wastewater from the HS system is routed directly to the aerobic biodigester unit 1260 via bypass stream 1243. Since anaerobic biodigester 1250 is offline, no biogas stream 1254 is produced to send to the HS system 1200.

Table 1 shows that for 100 parts $CO_2$ consumed in the operation of the eFuels plant, 26.8 parts of SMD (e.g., jet fuel) and 4.7 parts of SLD are produced with no $CO_2$ or criteria pollutants emitted.

Example 7

FIG. 7 depicts an eFuels plant without the RFCER system disclosed herein. There is no $H_2$ storage 1040, $CO_2$ storage 1080, or SLG storage 1210 and recycle 1212, 1214. Seawater desalination 1400, 1402, 1010, and 1012 is replaced by freshwater feed stream 1406 to electrolysis unit 1030. The OFH 1280 is replaced with fired heaters combusting fuel gas with air instead of oxygen. There is no electric start-up boiler associated with the steam turbine generator 1290. There is no anaerobic biodigester 1250 with all HS system 1200 process wastewater routed directly to the aerobic biodigester 1260. There are no heat integration facilities 1295 for low grade heat recovery and upgrading. Desalinated water is replaced with a fresh water feed stream 1406.

Process units and streams highlighted with dashed lines in FIG. 7 indicate process units and streams that are not present relative to base case Example 1.

Table 1 shows that for 104 parts $CO_2$ consumed in the operation of the eFuels plant, 25.9 parts of SMD (e.g., jet fuel) and 4.7 parts of SLD. However, 7.705E-03 parts of $CO_2$ and 1.932E-05 of criteria pollutants are emitted.

Table 1, above, shows that Examples 1-6 all produce more SMD than Example 7, while Examples 1-6 all have a lower feed rate of $CO_2$ than Example 7.

Table 2, below, summarizes environmental and energy performance parameters for Examples 1-7.

Carbon efficiency, as used herein, means carbon content in products divided by carbon content in feed. Higher carbon efficiency means less carbon emissions from the plant (air or liquid), giving the products the lowest possible carbon intensity. Even with the broad range of operating scenarios in Examples 1-6 with the integrated RFCER system disclosed herein, carbon efficiency ranges from 94.7% to 98.9%. In contrast, Example 7 without the integrated RFCER system demonstrates a carbon efficiency of 91.3%

Electricity is a limited resource, and even more so for an electrical grid powered by renewable energy sources. Higher electrical efficiency translates to higher production rates at constant electrical load and increased operational flexibility when electrical load is more limited. Electrical efficiency, as used herein, means energy content in products divided by plant electrical power consumed in operation of the eFuels plant. At times, hydrogen is supplied to the HS system from the hydrogen storage system, the electrolysis unit can run at reduced rates for a limited time or even be shut down for a short time, giving a higher electrical efficiency for the time period of reduced rates or shutdown, such as is demonstrated by Example 2. At other times, hydrogen production is maximized to send excess hydrogen above HS system feed requirements to the hydrogen storage system, resulting in a lower electrical efficiency, such as is demonstrated in Example 3. The net effect of using $H_2$ from storage during some time periods and filling the $H_2$ storage during other periods results in average electrical efficiency approximately equivalent to the base case electrical efficiency of Example 1, wherein hydrogen production and hydrogen feed rate to the HS system are the same. Even with the broad range of operating scenarios in Examples 1-6, electrical energy efficiency ranges from 32.2% to 154.0%. In contrast, Example 7 demonstrates an electrical energy efficiency of 34.7%. However, this broad range of operating scenarios allows very different instantaneous hydrogen production rates (i.e., different electrolyzer rates and corresponding electrical loads) while maintaining stable operations of the HS system. Without wishing to be bound by any particular theory, it is believed that this stability aspect of the RFCER system actually provides an effective long-term electrical efficiency that more than offsets the slightly higher electrical energy efficiency shown for Example 7 (i.e., inability of the process of Example 7 to efficiently manage fluctuations in the electrical grid).

Total energy efficiency, as used herein, means the sum of energy in eFuels products plus energy exported from the eFuels plant in exported heat divided by the electrical load consumed in operation of the eFuels plant to produce such products and heat exports. Even with the broad range of operating scenarios in Examples 1-6, total energy efficiency ranges from 32.2% to 260.3%. In contrast, Example 1 demonstrates a total energy efficiency of 57.7%, whereas Example 7 shows a total energy efficiency of 34.7%. This demonstrates a significant improvement in energy efficiency for the process described here when compared to the eFuels plant without the integrated RFCER system.

Carbon intensity is a measure of the $CO_2$ emitted over the product lifecycle (i.e., total SLG, SLD, SMD, and SHD exported from the eFuels plant). A high carbon intensity means the product lifecycle is increasing $CO_2$ in atmosphere. A zero carbon intensity means the product lifecycle is not adding or reducing $CO_2$ in atmosphere. A negative carbon intensity means the product is reducing atmospheric $CO_2$. Even with the broad range of operating scenarios in Examples 1-6, product carbon intensity in $CO_2$ consumed in the eFuels plant per tonne of synthetic hydrocarbon product ranges from 0 $CO_2$/t to 0.17 $CO_2$/t. In contrast, Example 7 demonstrates a product carbon intensity of 0.30 $CO_2$/t. Furthermore, Example 7 lacks the operating flexibility as shown by Examples 1-6. Therefore, the flow diagram of Example 7 does not have the ability to respond to fluctuations in power from the electrical grid without causing at least alteration of, and in some cases interruption of, the operation and production rates of the HS system.

TABLE 2

| Performance | | Example | | | | | | |
|---|---|---|---|---|---|---|---|---|
| Parameter | Units | 1 | 2 | 3 | 4 | 5 | 6 | 7 |
| Carbon Efficiency | % | 97.7 | 97.7 | 98.9 | 94.7 | 97.7 | 97.6 | 91.3 |
| Electrical Energy Efficiency | % | 34.1 | 154.0 | 32.6 | 33.4 | 32.2 | 34.1 | 34.7 |
| Total Energy Efficiency | % | 57.7 | 260.3 | 55.1 | 57.1 | 32.2 | 57.8 | 34.7 |
| Product Carbon Intensity | $CO_2$/t[1] | 0.07 | 0 | 0.03 | 0.17 | 0.07 | 0.08 | 0.30 |

[1]$CO_2$ emitted per tonne of eFuels products (combined production of SLG, SLD, SMD, and SHD exported from the eFuels plant) over the eFuel lifecycle In summary, the process of Example 1 reduces the electrical efficiency by 1.7% when compared to the process of Example 7, an eFuels plant without the RFCER system (i.e., 34.1/34.7=98.3%). However, the process of Example 1 increases total energy efficiency by 166% compared to the process of Example 7 (i.e., 57.7/34.7=166%), and improves (reduces) carbon intensity by 77% at the same time (i.e., 0.07/0.30=23%). Additionally, the use of seawater significantly reduces freshwater consumption/competition as described in Example 7. The process disclosed herein also reduces the pollutant emissions to the atmosphere. Overall, the process disclosed herein provides more efficient use of natural resources and minimizes environmental impact for the production and use of sustainable liquid hydrocarbons.

The scope of the present application is not intended to be limited to the particular embodiments of the processes, means, methods, and/or steps described in the specification. The particular embodiments disclosed above are illustrative only, as the process and system may be modified and practiced in different but equivalent manners apparent to those skilled in the art having the benefit of the teachings herein. Although the present invention and its advantages have been described in detail, it should be understood that various changes, substitutions and alterations can be made herein without departing from the spirit and scope of the invention as defined by the appended claims.

For the sake of brevity, only certain ranges are explicitly disclosed herein. However, in addition to recited ranges, any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All patents, test procedures, and other documents cited in this application are fully incorporated herein by reference for all jurisdictions in which such incorporation is permitted. In the event of conflict between one or more of the incorporated patents or publications and the present disclosure, the present specification, including definitions, controls.

What is claimed is:

1. A process for producing one or more synthetic hydrocarbon products, comprising:

a) adding a first amount of electrical load and a first corresponding water feed stream rate to an electrolysis unit under reaction conditions sufficient to form a first hydrogen stream and an oxygen stream, wherein the electrolysis unit:

i) comprises one or more alkaline electrolysis cells (AECs), one or more proton exchange membrane cells (PEMs), or a combination thereof; and ii) is capable of changing to a second amount of electrical load and a second corresponding water feed stream rate at a rate of change greater than or equal to 0.1%/sec, wherein 100% is the maximum electrical load of the electrolysis unit;

b) optionally receiving and storing a portion of the first hydrogen stream in a hydrogen storage system;

c) feeding at least a portion of the first hydrogen stream and a carbon dioxide stream to a hydrocarbon synthesis (HS) system, comprising a reverse water-gas shift (RWGS) reactor to convert a carbon dioxide feed stream and a first hydrogen feed stream to syngas as feed to a Fischer-Tropsch (FT) reactor to produce FT hydrocarbon products as feed to a hydrocracking reactor to produce a hydrocarbon product as feed to one or more distillation columns to separate the hydrocarbon product to produce one or more of synthetic liquefied gas (SLG), a synthetic light distillate (SLD), a synthetic middle distillate (SMD), and a synthetic heavy distillate (SHD);

d) in an oxygen-fired heater (OFH) comprising a combustion zone and a heating zone:

i) receiving combustion reactants in the combustion zone to produce heat and an OFH flue gas, comprising a first carbon dioxide stream and water, wherein the combustion reactants comprise a portion of the oxygen from the electrolysis unit and a gas stream, comprising HS system purge gas, HS system off gas, SLG, or a combination thereof, from the HS system; and ii) receiving at least one steam stream from the HS system in the heating zone to absorb a portion of the heat produced in the combustion zone to produce one or more superheated steam streams, and adding at least a portion of the one or more superheated steam streams to a steam turbine generator to produce generated electricity to supplement power requirements of the process for producing one or more synthetic hydrocarbon products and a steam condensate stream as additional feed to a demineralization unit; and e) optionally receiving at least a portion of the first carbon dioxide stream in a carbon dioxide compression and storage system;

f) recovering the one or more synthetic hydrocarbon products comprising the synthetic liquefied gas (SLG), the synthetic light distillate (SLD), the synthetic middle distillate (SMD), and the synthetic heavy distillate (SHD);

wherein the first hydrogen feed stream comprises a first portion of the first hydrogen stream, a second hydrogen stream withdrawn from the hydrogen storage and compression system, or a combination thereof; and the carbon dioxide feed stream comprises a portion of the first carbon dioxide stream, a second carbon dioxide stream withdrawn from the carbon dioxide storage and compression system, or a combination thereof.

2. The process of claim 1, wherein the first and second amounts of electricity are provided by an electrical grid powered by one or more renewable energy sources.

3. The process of claim 2, wherein the one or more renewable energy sources comprise solar energy, wind energy, hydroelectric energy, geothermal energy, biomass combustion, nuclear energy, tidal energy, wave energy, hydrogen fuel cells, seawater fuel cells, or a combination thereof.

4. The process of claim 1, wherein the carbon dioxide stream comprises:

a) carbon dioxide imported from a source external to the process;

b) carbon dioxide produced with a direct air capture unit;

c) carbon dioxide produced with an anaerobic biodigester;

d) carbon dioxide produced as a combustion product of the oxygen-fired heater;

e) carbon dioxide withdrawn from the carbon dioxide compression and storage system; or f) a combination thereof.

5. The process of claim 1, wherein the process further comprises introducing at least a portion of the synthetic liquefied gas (SLG) to a SLG storage facility.

6. The process of claim 5, wherein a SLG stream is withdrawn from the SLG storage facility, recycled from the HS system, or a combination thereof, as feed to the HS system.

7. The process of claim 1, wherein the process further comprises:

a) adding sea water to a thermal desalination unit under desalination conditions to produce a desalinated water effluent, wherein the thermal desalination unit is heat integrated with the electrolysis unit;

b) adding the desalinated water effluent to the demineralization unit under demineralization conditions to produce a demineralized water effluent; and c) withdrawing a first portion of the demineralized water effluent as the water feed stream to the electrolysis unit.

8. The process of claim 7, wherein the process further comprises:

a) adding a second portion of the demineralized water effluent to a deaeration unit to produce a boiler feed water stream; and b) sending the boiler feed water stream to the hydrocarbon synthesis system as a cooling medium for one or more process units in the hydrocarbon synthesis system.

9. The process of claim 8, wherein the cooling medium is converted to one or more steam streams in the HS system.

10. The process of claim 1, further comprising adding at least a portion of the combustion product to the combustion zone to control the temperature of the combustion zone.

11. The process of claim 1, further comprising recovering water from the combustion product.

12. The process of claim 1, further comprising sending at least a portion of the one or more superheated steam streams to the HS system to provide heat to one or more process units in the HS system.

13. The process of claim 1, further comprising:

a) adding a process wastewater stream to an anaerobic biodigester, wherein the process wastewater stream comprises a first organic material;

b) implementing anaerobic biodigestion conditions in the anaerobic biodigester;

c) withdrawing a first gas product stream and a first treated water stream, wherein the first gas product stream comprises carbon dioxide, methane, or a combination thereof; and d) adding the first gas product stream to:

i) the hydrocarbon synthesis system as feed to one or more units in the HS system;

ii) the oxygen-fired heater as a combustion reactant; or iii) a combination thereof.

14. The process of claim 13, further comprising:

a) adding the first treated water stream from the anaerobic biodigester to an aerobic biodigester, wherein the first treated water stream comprises a second organic material;

b) implementing aerobic biodigestion conditions in the aerobic biodigester;

c) withdrawing a second treated water stream and a digestate solid; and d) adding the second treated water stream as additional feed to a thermal desalination unit.

15. The process of claim 14, further comprising;

a) recovering an amount of excess heat from the electrolysis unit, the stream turbine generator, or a combination thereof; and b) delivering at least a portion of the amount of excess heat to the thermal desalination unit, the direct air capture unit, an export disposition, or a combination thereof.

16. The process of claim 15, wherein recovering and/or delivering are implemented in a heat integration system comprising one or more heat pumps.

17. The process of claim 1, wherein the process operates with a carbon efficiency of greater than or equal to 94.7%, wherein carbon efficiency is the carbon content in products divided by the carbon content in feed.

18. An eFuels production system, comprising:

a) an electrolysis unit to react electricity and a water feed stream in the presence of an electrolysis catalyst to form a first hydrogen stream and an oxygen stream, wherein the electrolysis unit:

i) comprises one or more alkaline electrolysis cells (AECs), one or more proton exchange membrane cells (PEMs), or a combination thereof; and ii) is capable of changing from a first amount of electrical load to a second amount of electrical load and from a first amount of water feed rate, corresponding to the first amount of electrical load, to a second amount of water feed rate, corresponding to the second amount of electrical load, at a rate of change greater than or equal to 0.1%/sec, wherein 100% is the maximum electrical load of the electrolysis unit;

b) a hydrogen storage system to optionally receive and store a portion of the first hydrogen stream;

c) a hydrocarbon synthesis (HS) system, comprising a reverse water-gas shift (RWGS) reactor to convert a carbon dioxide feed stream and a first hydrogen feed stream to syngas as feed to a Fischer-Tropsch (FT) reactor to produce FT hydrocarbon products as feed to a hydrocracking reactor to produce a hydrocarbon product as feed to one or more distillation columns to separate the hydrocarbon product to produce one or more of synthetic liquefied gas (SLG), a synthetic light distillate (SLD), a synthetic middle distillate (SMD), and a synthetic heavy distillate (SHD);

d) an oxygen-fired heater (OFH), the OFH comprising a combustion zone and a heating zone, the OFH adapted for:

i) receiving combustion reactants in the combustion zone to produce heat and an OFH flue gas, comprising a first carbon dioxide stream and water, wherein the combustion reactants comprise a portion of the oxygen from the electrolysis unit and a gas stream, comprising HS system purge gas, HS system off gas, SLG, or a combination thereof, from the HS system; and ii) receiving at least one steam stream from the HS system in the heating zone to absorb a portion of the heat produced in the combustion zone to produce a superheated steam stream, which is introduced to a steam turbine generator to produce generated electricity to supplement power requirements of the eFuels production system and a steam condensate stream processed for use as additional water feed to the electrolysis unit; and e) a carbon dioxide compression and storage system configured to receive at least a portion of the first carbon dioxide stream;

wherein the first hydrogen feed stream comprises a first portion of the first hydrogen stream, a second hydrogen stream withdrawn from the hydrogen storage and compression system, or a combination thereof; and the carbon dioxide feed stream comprises a portion of the first carbon dioxide stream, a second carbon dioxide stream withdrawn from the carbon dioxide storage and compression system, or a combination thereof.

19. The system of claim 18, further comprising a synthetic liquefied gas (SLG) compression and storage system to supply SLG to the HS system.

20. The system of claim 18, further comprising a direct air capture (DAC) unit to recover carbon dioxide from the atmosphere, wherein the first carbon dioxide feed stream comprises the recovered carbon dioxide, the recovered carbon dioxide is added to the carbon dioxide storage and compression system, or a combination thereof.

21. The system of claim 18, further comprising:

a thermal desalination unit to treat sea water to produce a desalinated water effluent, wherein the thermal desalination unit is heat integrated with the electrolysis unit; and a demineralization unit to treat the desalinated water effluent to produce the water feed stream.

22. The system of claim 18, further comprising:

a) an anaerobic biodigester to receive a process wastewater stream from the HS system to produce a gas stream and a first treated water stream, wherein the gas stream is recycled to the HS system; and b) an aerobic biodigester for receiving the process wastewater stream or the first treated water stream and producing a second treated water stream to be sent as additional feed to a thermal desalination unit.

23. The system of claim 18, further comprising:

a) a direct air capture (DAC) unit to recover carbon dioxide from the atmosphere to produce carbon dioxide as a separate stream to the HS system, the carbon dioxide compression and storage system, or a combination thereof;

b) a thermal desalination unit to treat sea water to produce a desalinated water effluent, wherein the thermal desalination unit is heat integrated with the electrolysis unit; and c) a demineralization unit to treat the desalinated water effluent to produce the water feed stream.

24. The system of claim 18, further comprising:

a) a thermal desalination unit to treat sea water to produce a desalinated water effluent, wherein the thermal desalination unit is heat integrated with the electrolysis unit;

b) a demineralization unit to treat the desalinated water effluent to produce the water feed stream; and c) an anaerobic biodigester to receive a process wastewater stream from the HS system to produce a gas stream and a first treated water stream, wherein the gas stream is recycled to the HS system; and/or an aerobic biodigester for receiving the process wastewater stream or the first treated water stream and producing a second treated water stream to be sent as additional feed to the thermal desalination unit.

25. The system of claim 18, further comprising:

a) a direct air capture (DAC) unit to recover carbon dioxide from the atmosphere to produce carbon dioxide as a separate stream to the HS system, the carbon dioxide compression and storage system, or a combination thereof; and b) an anaerobic biodigester to receive a process wastewater stream from the HS system to produce a gas stream and a first treated water stream, wherein the gas stream is recycled to the HS system; and/or an aerobic biodigester for receiving the process wastewater stream or the first treated water stream and producing a second treated water steam to be sent as additional feed to a thermal desalination unit.

26. The system of claim 18, wherein:

the second amount of electrical load is less than the first amount of electrical load; and hydrogen is withdrawn from the hydrogen storage system to offset a loss of hydrogen production resulting from the reduced electrical and maintain a hydrogen flow to the HS system equivalent to the first portion of the hydrogen stream.

27. The system of claim 18, wherein the oxygen-fired heater is the only process unit in the eFuels system configured to receive oxygen from the electrolysis unit.

28. The system of claim 18, wherein the HS system is configured to receive the carbon dioxide feed stream from one or more sources from the group consisting of carbon dioxide:

a) imported from a source external to the system;

b) produced with a direct air capture unit;

c) withdrawn from an anaerobic biodigester;

d) produced as a combustion product of the oxygen-fired heater; and e) withdrawn from the carbon dioxide storage and compression system.

29. The system of claim 18, wherein the system is configured to operate with a carbon efficiency of greater than or equal to 94.7%, wherein carbon efficiency is the carbon content in products divided by the carbon content in feed.

* * * * *